(12) United States Patent
Jeganathan et al.

(10) Patent No.: US 7,060,425 B1
(45) Date of Patent: Jun. 13, 2006

(54) COLOR PHOTOGRAPHIC MATERIAL

(75) Inventors: Suruliappa Gowper Jeganathan, Glen Mills, PA (US); Stéphan Biry, Village-Neuf (FR); Peter Nesvadba, Marly (CH); David George Leppard, Marly (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 417 days.

(21) Appl. No.: 09/806,360

(22) PCT Filed: Oct. 11, 1999

(86) PCT No.: PCT/EP99/07616

§ 371 (c)(1),
(2), (4) Date: Mar. 29, 2001

(87) PCT Pub. No.: WO00/23849

PCT Pub. Date: Apr. 27, 2000

(30) Foreign Application Priority Data

| Oct. 19, 1998 | (EP) | ................................. 98811035 |
| Jun. 11, 1999 | (EP) | ................................. 99810514 |
| Jul. 9, 1999 | (EP) | ................................. 99810612 |

(51) Int. Cl.
*G03C 1/34* (2006.01)

(52) U.S. Cl. ...................... 430/543; 430/544; 430/546; 430/551; 430/607; 430/614; 524/100; 524/109; 544/238; 544/239; 544/347; 546/153; 549/13; 549/23

(58) Field of Classification Search ................ 430/543, 430/544, 546, 551, 600, 614; 524/107, 109; 544/238, 239, 347; 546/153; 549/13, 23
See application file for complete search history.

(56) References Cited

U.S. PATENT DOCUMENTS

| 3,615,521 A | 10/1971 | Oftedahl, Jr. ................... 96/66 |
| 3,703,375 A | 11/1972 | Salminen ..................... 96/56.4 |
| 4,325,863 A * | 4/1982 | Hinsken et al. .............. 624/111 |
| 4,338,244 A * | 7/1982 | Hinsken et al. .............. 524/109 |
| 4,366,240 A | 12/1982 | Lassig et al. ................ 430/542 |
| 4,611,016 A | 9/1986 | Hinsken et al. ................ 529/99 |
| 5,073,448 A | 12/1991 | Vieira et al. ................. 428/331 |
| 5,300,414 A | 4/1994 | Leppard et al. .............. 430/507 |
| 5,428,162 A | 6/1995 | Nesvadba .................... 544/221 |
| 5,538,840 A | 7/1996 | Van Toan et al. ............. 430/5.2 |
| 5,578,437 A | 11/1996 | Asami et al. ................. 430/558 |
| 5,597,854 A * | 1/1997 | Birbaum et al. ............. 524/100 |
| 5,607,624 A | 3/1997 | Nesvadba et al. ........... 252/589 |
| 5,668,200 A | 9/1997 | Valet et al. .................. 524/100 |
| 5,686,633 A | 11/1997 | Vieira et al. ................. 549/434 |
| 5,780,625 A | 7/1998 | Jeganathan et al. ........ 544/58.2 |
| 5,814,692 A | 9/1998 | Nesvadba .................... 524/107 |
| 5,981,160 A | 11/1999 | Odenwälder et al. ....... 430/551 |

FOREIGN PATENT DOCUMENTS

| DE | 197 28 214 | 1/1998 |
| DE | 197 49 083 | 7/1998 |
| EP | 0 560 198 | 9/1993 |
| EP | 0 591 102 | 9/1993 |
| EP | 589839 | * 9/1993 |
| EP | 0 648 765 | 9/1994 |
| EP | 0 711 804 | 11/1995 |
| EP | 0 871 066 | 3/1998 |
| GB | 2042562 | 9/1980 |

(Continued)

OTHER PUBLICATIONS

T.H.James, "The Theory of the Photographic Process", 4th Edition, pp. 393-399 (1977).*

(Continued)

*Primary Examiner*—Amanda Walke
(74) *Attorney, Agent, or Firm*—Tyler A. Stevenson

(57) ABSTRACT

A color photographic material is described containing a compound of formula (I) wherein, if n=1, $R_1$ is, inter alia, a radical of formula (II), and, if n=2, $R_1$ is unsubstituted or $C_1$–$C_4$alkyl- or hydroxy-substituted phenylene or naphthylene; or —$R_{12}$—X—$R_{13}$—, and other residues are as defined in claim 1. The compound of formula (I) is effective as scavenger of the oxidized form of the developer (Dox scavenger), especially when contained in an interlayer between light sensitive layers. Selected compounds of this class can also be used as additives, for example as dye stabilizer, in color photographic materials, or as an antioxidant for organic materials.

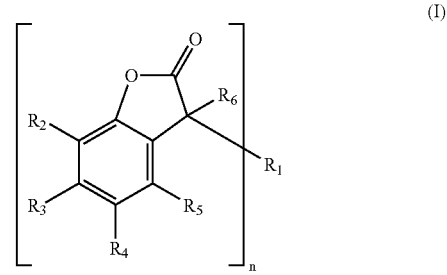

(I)

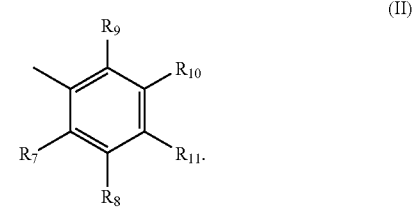

(II)

13 Claims, No Drawings

FOREIGN PATENT DOCUMENTS

| | | |
|---|---|---|
| GB | 2 267 088 | 11/1993 |
| GB | 2 267 490 | 12/1993 |
| GB | 2 267 491 | 12/1993 |
| GB | 2281910 | 3/1995 |
| GB | 2 294 043 | 4/1996 |
| GB | 2 315 070 | 1/1998 |
| GB | 2 322 374 | 8/1998 |
| GB | 2 322 861 | 9/1998 |
| WO | 80/01566 | 8/1980 |
| WO | WO 94/12501 * | 6/1994 |

OTHER PUBLICATIONS

Derw. Abst. 98-400233/35 of DE 197 49 083 (1998).

D. R. Shridhar et al., Indian Journal of Chemistry, vol. 19B, (1980) pp. 891-894.

* cited by examiner

COLOR PHOTOGRAPHIC MATERIAL

The present invention relates to colour photographic material comprising a certain lactone (benzofuran-2-one) type compound, to the use of this compound as an additive to photographic material, especially as scavenger for the oxidised form of the developer (Dox-scavenger), to some new compounds of the benzofuran-2-one class, and their use as stablisers for organic material against oxidative, thermal and/or light-induced degradation.

It is well known that one of the problems associated with colour photography is the diffusion of the oxidised colour developer away from the light sensitive silver halide emulsion layer in which it is formed into another silver halide emulsion layer, which can result in the formation of unwanted dyes at undesired places. For instance, while being generated in the green sensitive layer and forming a magenta dye through a coupling reaction with the incorporated magenta coupler, the oxidised developer can also diffuse to the red sensitive layer thereby producing unwanted cyan dye or to the blue sensitive layer thereby producing unwanted yellow dye. This kind of colour formation in the wrong layers will damage the colour balance of the photographic image and thus result in poor colour reproduction. One way of circumventing this problem is to incorporate oxidised developer scavengers in interlayers between the light sensitive silver halide emulsion layers. These scavengers should have additional properties such as low tendency to migrate, good stability towards aerial oxidation and high solubility in photographic oils.

Several classes of compounds that are useful as scavengers for oxidised developers are known in literature, e.g. specific derivatives of hydroquinone (EP-A-560198), or compounds of the classes sulphonamidophenol, gallic acid, resorcinol, catechol, aminophenol or aminonaphthol; or natural antioxidants such as vitamin E or vitamin C.

Some compounds of the class benzofuran-2-one are described in U.S. Pat. No. 4,611,016 or U.S. Pat. No. 5,814,692 and publications cited therein. Photographic material containing a certain type of benzofuran-2-one is mentioned in U.S. Pat. No. 3,615,521 (use as precursors of photographic developing agent) and in U.S. Pat. No. 4,336,240 (hydroxy substituted compounds as electron donor precursors for reducible colour providing compounds). EP-A-871066 mentions the use of a symmetrically substituted 3-(2-hydroxyphenyl)-benzofuran-2-one in the interlayer of a colour photographic material.

It has now been found that certain compounds of the 3-aryl-benzofuran-2-one class are especially useful as additives to photographic material. They are effective in a number of applications and find utility, for example, as scavengers for the oxidised developer (also termed hereafter Dox scavengers), as dye stabilisers, as antioxidants or as antifoggants. Liquid compounds of the below formula I can also be used as a photographic oil. These compounds are especially stable towards aerial oxidation, diffusion fast and also exhibits a good solubility in high boiling photographic oils. They are well suited for use in photographic elements containing pyrazolotriazole couplers as magenta dye providing compounds, since they are harmless to the light fastness of magenta images obtained from such pyrazolotriazole couplers when compared to hydroquinones.

Primary subject of the invention is a process for preventing migration of the oxidised developer in a colour photographic material from one colour sensitive layer to another by incorporating a compound of the formula I into said material

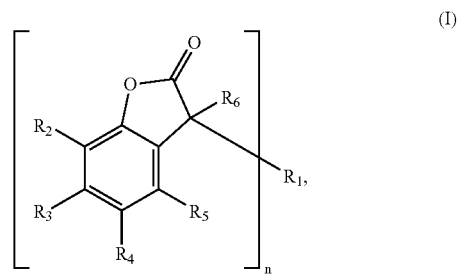

wherein, if n=1,

R$_1$ is a cyclic residue selected from naphthyl, phenanthryl, anthryl, 5,6,7,8-tetrahydro-2-naphthyl, 5,6,7,8-tetrahydro-1-naphthyl, thienyl, benzo[b]thienyl, naphtho[2,3-b]thienyl, thianthrenyl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by $C_1$–$C_4$alkyl, $C_1$–$C_4$alkoxy, $C_1$–$C_4$alkylthio, hydroxy, halogen, amino, $C_1$–$C_4$alkylamino, phenylamino or di($C_1$–$C_4$-alkyl)amino; or R$_1$ is a radical of formula II

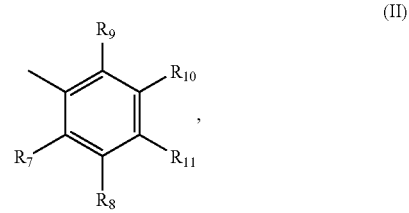

and, if n=2,

R$_1$ is unsubstituted or $C_1$–$C_4$alkyl- or hydroxy-substituted phenylene or naphthylene; or —R$_{12}$—X—R$_{13}$—;

R$_2$, R$_3$, R$_4$ and R$_5$ are each independently of one another hydrogen; chloro; hydroxy; $C_1$–$C_{25}$alkyl; $C_7$–$C_9$phenylalkyl; unsubstituted or $C_1$–$C_4$alkyl-substituted phenyl; unsubstituted or $C_1$–$C_4$alkyl-substituted $C_5$–$C_8$cycloalkyl; $C_1$–$C_{18}$alkoxy; $C_1$–$C_{18}$alkylthio; $C_1$–$C_4$alkylamino; di($C_1$–$C_4$-alkyl)amino; $C_1$–$C_{25}$alkanoyloxy; $C_1$–$C_{25}$alkanoylamino; $C_3$–$C_{25}$alkenoyloxy; $C_3$–$C_{25}$alkanoyloxy which is interrupted by oxygen, sulphur or

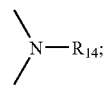

$C_6$–$C_9$cycloalkylcarbonoyloxy; benzoyloxy or $C_1$–$C_{12}$alkyl-substituted benzoyloxy; or R$_2$ and R$_3$, or R$_3$ and R$_4$, or R$_4$ and R$_5$, together with the linking carbon atoms, form a benzene ring;

or $R_4$ is $-C_mH_{2m}-COR_{15}$, $-O-(C_vH_{2v})-COR'_{15}$, $-O-(CH_2)_q-OR_{32}$, $-OCH_2-CH(OH)-CH_2-R'_{15}$, $-OCH_2-CH(OH)-CH_2-OR_{32}$, or $-(CH_2)_q$ OH;

or, if $R_3$, $R_5$ and $R_6$ are hydrogen, $R_4$ is additionally a radical of formula III

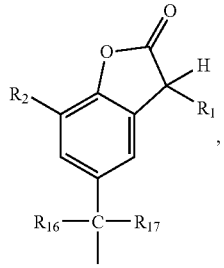

(III)

wherein $R_1$ is as defined above for n=1;

$R_6$ is hydrogen, or, when $R_4$ is hydroxy, $R_6$ can also be $C_1-C_{25}$alkyl or $C_3-C_{25}$alkenyl;

$R_7$, $R_8$, $R_9$, $R_{10}$ and $R_{11}$ are each independently of one another hydrogen; halogen; hydroxy; $C_1-C_{25}$alkyl; $C_2-C_{25}$alkyl which is interrupted by oxygen, sulphur or

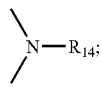

$C_1-C_{25}$alkoxy; $C_2-C_{25}$alkoxy which is interrupted by oxygen, sulphur or

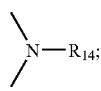

$C_1-C_{25}$alkylthio; $C_3-C_{25}$-alkenyl; $C_3-C_{25}$alkenyloxy; $C_3-C_{25}$alkynyl; $C_3-C_{25}$alkynyloxy; $C_7-C_9$phenylalkyl; $C_7-C_9$phenylalkoxy; unsubstituted or $C_1-C_4$alkyl-substituted phenyl; unsubstituted or $C_1-C_4$alkyl-substituted phenoxy; unsubstituted or $C_1-C_4$alkyl-substituted $C_5-C_8$cycloalkyl; unsubstituted or $C_1-C_4$alkyl-substituted $C_5-C_8$cycloalkoxy; $C_1-C_4$alkylamino; di($C_1-C_4$alkyl)amino; $C_1-C_{25}$alkanoyl; $C_3-C_{25}$alkanoyl which is interrupted by oxygen, sulphur or

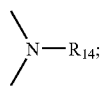

$C_1-C_{25}$alkanoyloxy; $C_3-C_{25}$alkanoyloxy which is interrupted by oxygen, sulphur or

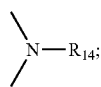

$C_1-C_{25}$alkanoylamino; $C_3-C_{25}$alkenoyl; $C_3-C_{25}$alkenoyl which is interrupted by oxygen, sulphur or

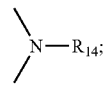

$C_3-C_{25}$alkenoyloxy; $C_3-C_{25}$alkenoyloxy which is interrupted by oxygen, sulphur or

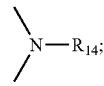

$C_6-C_9$cycloalkylcarbonyl; $C_6-C_9$cycloalkylcarbonyloxy; benzoyl or $C_1-C_{12}$alkyl-substituted benzoyl; benzoyloxy or $C_1-C_{12}$alkyl-substituted benzoyloxy;

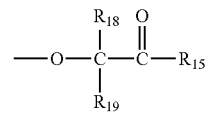

or

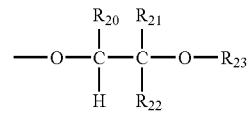

or, in formula II, $R_7$ and $R_8$, or $R_8$ and $R_{11}$, together with the linking carbon atoms, form a benzene ring;

$R_{12}$ and $R_{13}$ are each independently of the other unsubstituted or $C_1-C_4$alkyl-substituted phenylene or naphthylene;

$R_{14}$ is hydrogen or $C_1-C_8$alkyl;

$R_{15}$ and $R'_{15}$ independently are hydroxy;

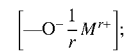

$C_1-C_{20}$alkoxy; $C_3-C_{20}$alkoxy interrupted by O and/or substituted by a radical selected from OH, phenoxy, $C_7-C_{15}$alkylphenoxy, $C_7-C_{15}$alkoxyphenoxy; or are $C_5-C_{12}$cycloalkoxy; $C_7-C_{17}$phenylalkoxy; phenoxy;

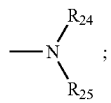

or a group of the formula IIIa or IIIb

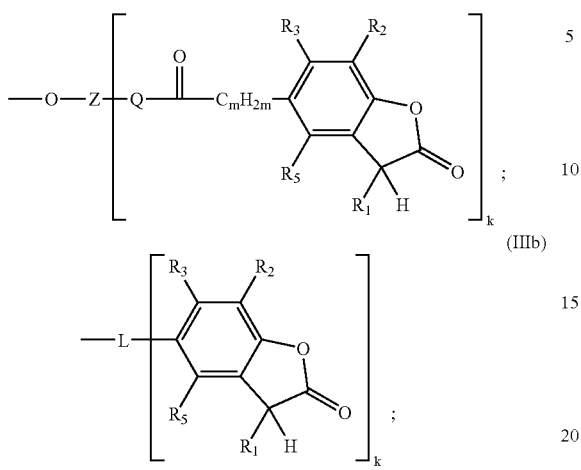

R$_{16}$ and R$_{17}$ are each independently of the other hydrogen, CF$_3$, C$_1$–C$_{12}$alkyl or phenyl, or R$_{16}$ and R$_{17}$, together with the linking carbon atom, are a C$_5$–C$_8$cycloalkylidene ring which is unsubstituted or substituted by 1 to 3 C$_1$–C$_4$alkyl;

R$_{18}$ and R$_{19}$ are each independently of the other hydrogen, C$_1$–C$_4$alkyl or phenyl;

R$_{20}$ is hydrogen or C$_1$–C$_4$alkyl;

R$_{21}$ is hydrogen; unsubstituted or C$_1$–C$_4$alkyl-substituted phenyl; C$_1$–C$_{25}$alkyl; C$_2$–C$_{25}$alkyl which is interrupted by oxygen, sulphur or

C$_7$–C$_9$phenylalkyl which is unsubstituted or substituted at the phenyl moiety by 1 to 3 C$_1$–C$_4$alkyl; C$_7$–C$_{25}$phenylalkyl which is interrupted by oxygen, sulphur or

and which is unsubstituted or substituted at the phenyl moiety by 1 to 3 C$_1$–C$_4$alkyl; or R$_{20}$ and R$_{21}$, together with the linking carbon atoms, form a C$_5$–C$_{12}$cycloalkylene ring which is unsubstituted or substituted by 1 to 3 C$_1$–C$_4$alkyl;

R$_{22}$ is hydrogen or C$_1$–C$_4$alkyl;

R$_{23}$ is hydrogen; C$_1$–C$_{25}$alkanoyl; C$_3$–C$_{25}$alkenoyl; C$_3$–C$_{25}$alkanoyl which is interrupted by oxygen, sulphur or

C$_2$–C$_{25}$alkanoyl which is substituted by a di(C$_1$–C$_6$alkyl)phosphonate group; C$_6$–C$_9$cycloalkylcarbonyl; thenoyl; furoyl; benzoyl or C$_1$–C$_{12}$alkyl-substituted benzoyl;

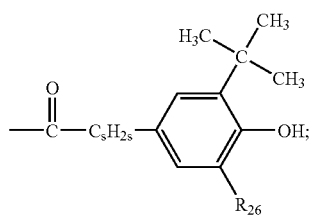

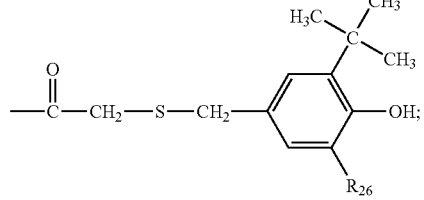

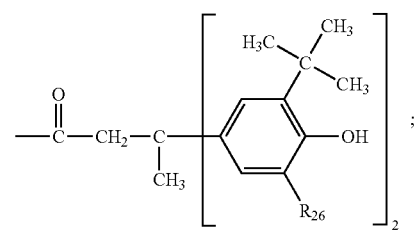

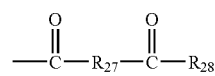

or

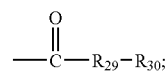

R$_{24}$ and R$_{25}$ are each independently of the other hydrogen or C$_1$–C$_{18}$alkyl;

R$_{26}$ is hydrogen or C$_1$–C$_8$alkyl;

R$_{27}$ is a direct bond; C$_1$–C$_{18}$alkylene; C$_2$–C$_{18}$alkylene which is interrupted by oxygen, sulphur or

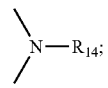

$C_2$–$C_{18}$alkenylene; $C_2$–$C_{20}$alkylidene; $C_7$–$C_{20}$phenylalkylidene; $C_5$–$C_8$cycloalkylene; $C_7$–$C_8$bicycloalkylene; unsubstituted or $C_1$–$C_4$alkyl-substituted phenylene;

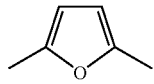

or

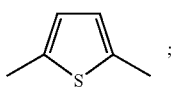

$R_{28}$ is hydroxy,

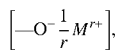

$C_1$–$nC_{18}$alkoxy or

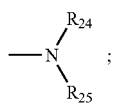

$R_{29}$ is oxygen or —NH—;
$R_{30}$ is $C_1$–$C_{18}$alkyl or phenyl;
$R_{31}$ is hydrogen or $C_1$–$C_{18}$alkyl;
$R_{32}$ is $C_1$–$C_{18}$alkanoyl; $C_1$–$C_8$alkanoyl substituted by phenyl or $C_7$–$C_{15}$alkylphenyl; $C_3$–$C_{18}$alkenoyl; cyclohexylcarbonyl; or naphthylcarbonyl;
L is a linking group of valency (k+1) and is as a divalent group —O—; Q—$C_2$–$C_{12}$alkylene-Q; —O—$CH_2$—CH(OH)—$CH_2$—O—; —Q—$C_2$–$C_{12}$alkylene-Q—CO—$C_vH_{2v}$—O—; —O—$C_2$–$C_{12}$alkylene-O—$CH_2$—CH(OH)—$CH_2$—O—; Q-interrupted Q—$C_4$–$C_{12}$alkylene-Q; Q-phenylene-Q or Q-phenylene-D-phenylene-Q with D being $C_1$–$C_4$alkylene, O, S, SO or $SO_2$;
L as a trivalent group is Q-capped $C_3$–$C_{12}$alkanetriyl, a trivalent residue of a hexose or a hexitol, or a group (—O—$CH_2$)$_3$C—$CH_2$OH; —Q—$C_aH_{2a}$—N($C_bH_{2b}$—Q—)—$C_cH_{2c}$—Q—; —Q—$C_3$–$C_{12}$alkanetriyl(—Q—CO—$C_vH_{2v}$—O—)$_2$; —O—$C_3$–$C_{12}$alkanetriyl(—O—$CH_2$—CH(OH)—$CH_2$—O—)$_2$; and
L as a tetravalent group is a tetravalent residue of a hexose or a hexitol; —Q—$C_4$–$C_{12}$alkanetetryl(—Q—CO—$C_vH_{2v}$—O—)$_3$; —O—$C_4$–$C_{12}$alkanetetryl(—O—$CH_2$—CH(OH)—$CH_2$—O—)$_3$; Q-capped $C_4$–$C_{12}$alkanetetryl; a group

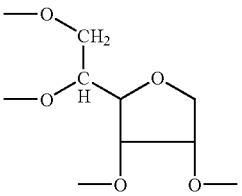

or a group

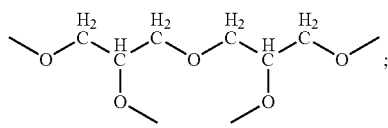

M is an r-valent metal cation;
Q is oxygen or —NH—;
X is a direct bond, oxygen, sulphur or —$NR_{31}$—;
Z is a linking group of valency (k+1) and is as a divalent group $C_2$–$C_{12}$alkylene; Q-interrupted $C_4$–$C_{12}$alkylene; phenylene or phenylene-D-phenylene with D being $C_1$–$C_4$alkylene, O, S, SO or $SO_2$;
Z as a trivalent group is $C_3$–$C_{12}$alkanetriyl, a trivalent residue of a hexose or a hexitol, a group (—$CH_2$)$_3$C—$CH_2$OH, or a group —$C_aH_{2a}$—N($C_bH_{2b}$—)—$C_cH_{2c}$—; and
Z as a tetravalent group is a tetravalent, carbon-ended residue of a hexose or a hexitol, $C_4$–$C_{12}$alkanetetryl, a group

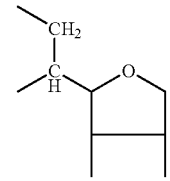

or a group

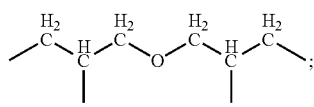

a, b, c and k independently are 1, 2 or 3;
m is 0 or a number from the range 1–12, preferably 1–6;
n is 1 or 2;
q is 1, 2, 3, 4, 5 or 6;
r is 1, 2 or 3; and
s is 0, 1 or 2;
v is 1, 2, 3, 4, 5, 6, 7 or 8, preferably 1 or 2;
provided that, when $R_7$ is hydroxy, alkanoyloxy or alkanoyloxy interrupted by O, S or N($R_{14}$) and $R_9$ is hydrogen, $R_{10}$ is not identical with $R_4$; and when $R_9$ is hydroxy, alkanoyloxy or alkanoyloxy interrupted by O, S or N($R_{14}$) and $R_7$ is hydrogen, $R_8$ is not identical with $R_4$.

Of certain technical interest is a process, where in the compound of formula I $R_2$, $R_3$, $R_4$ and $R_5$ are each independently of one another hydrogen, chloro, hydroxy, C₁–C₂₅alkyl, C₇–C₉phenylalkyl, unsubstituted or C₁–C₄alkyl-substituted phenyl; unsubstituted or C₁–C₄alkyl-substituted C₅–C₈cycloalkyl; C₁–C₁₈alkoxy, C₁–C₁₈alkylthio, C₁–C₄alkylamino, di(C₁–C₄-alkyl)amino, C₁–C₂₅alkanoyloxy, C₁–C₂₅alkanoylamino, C₃–C₂₅alkenoyloxy; C₃–C₂₅alkanoyloxy which is interrupted by oxygen, sulfur or

C₆–C₉cycloalkylcarbonyloxy, benzoyloxy or C₁–C₁₂alkyl-substituted benzoyloxy; or R₂ and R₃, or R₃ and R₄, or R₄ and R₅, together with the linking carbon atoms, form a benzene ring; or R₄ is —C_mH_{2m}—COR₁₅ or —(CH₂)_qOH or, if R₃, R₅ and R₆ are hydrogen, R₄ is additionally a radical of formula III; and R₁₅ is hydroxy,

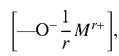

C₁–C₂₀alkoxy,

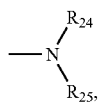

or a group of the formula IIIa.

R₁ is preferably a radical of formula II. These preferred compounds of formula I advantageously carry at least one hydrocarbon or substituted hydrocarbon radical R₂, R₃, R₄, R₅, R₇, R₈, R₉, R₁₀ and/or R₁₁, where the total number of carbon atoms in all radicals together is at least 3. More preferred compounds comprise one or more substituents among R₂–R₅ and R₇–R₁₁, wherein the total number of carbon atoms in all substituents together is 4–35, especially 7–30.

In preferred compounds of formula I, R₇ and R₉ are each independently of one another hydrogen; halogen; C₁–C₂₅alkyl; C₂–C₂₅alkyl which is interrupted by oxygen, sulphur or

C₂–C₂₅alkoxy which is interrupted by oxygen, sulphur or

C₁–C₂₅alkylthio; C₃–C₂₅alkenyl; C₃–C₂₅alkenyloxy; C₃–C₂₅alkynyl; C₃–C₂₅alkynyloxy; C₇–C₉phenylalkyl;

C₇–C₉phenylalkoxy; unsubstituted or C₁–C₄alkyl-substituted phenyl; unsubstituted or C₁–C₄alkyl-substituted phenoxy; unsubstituted or C₁–C₄alkyl-substituted C₅–C₈cycloalkyl; unsubstituted or C₁–C₄alkyl-substituted C₅–C₈cycloalkoxy; C₁–C₄alkylamino; di(C₁–C₄alkyl)amino; C₁–C₂₅alkanoyl; C₃–C₂₅alkanoyl which is interrupted by oxygen, sulphur or

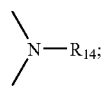

C₁–C₂₅alkanoylamino; C₃–C₂₅alkenoyl; C₃–C₂₅alkenoyl which is interrupted by oxygen, sulphur or

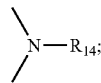

C₆–C₉cycloalkylcarbonyl; benzoyl or C₁–C₁₂alkyl-substituted benzoyl;

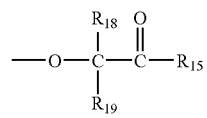

or

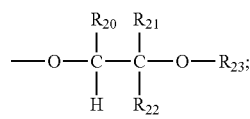

more preferably, R₇ and R₉ are hydrogen; halogen; C₁–C₂₅alkyl; C₂–C₂₅alkyl which is interrupted by oxygen, sulphur or

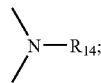

C₃–C₂₅-alkenyl; C₃–C₂₅alkynyl; C₇–C₉phenylalkyl; unsubstituted or C₁–C₄alkyl-substituted phenyl; unsubstituted or C₁–C₄alkyl-substituted C₅–C₈cycloalkyl;

most preferably, R₇ and R₉ are hydrogen; halogen, C₁–C₂₅alkyl; C₃–C₂₅-alkenyl; C₃–C₂₅alkynyl; C₇–C₉phenylalkyl; unsubstituted or C₁–C₄alkyl-substituted phenyl; unsubstituted or C₁–C₄alkyl-substituted C₅–C₈cycloalkyl; especially hydrogen, chloro or C₁–C₁₈alkyl.

R₈, R₁₀ and R₁₁ are often as defined above for R₇ and R₉ in the preferred compounds of formula I, or one of these residues, especially R₁₁, is OH, C₁–C₂₅alkoxy, phenyl, di(C₁–C₄alkylamino, C₁–C₂₅alkanoyloxy, or

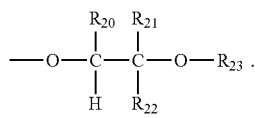

Further objects of the invention are the use of a compound of the formula I in colour photographic material, especially as Dox-scavenger, and a photographic material containing a compound of the formula I, especially as herein defined below, e.g. of formula IV.

$R_1$ may be, for example, the cyclic residue defied above which is unsubstituted or substituted by $C_1$–$C_4$alkyl, $C_1$–$C_4$alkoxy, $C_1$–$C_4$alkylthio, hydroxy, halogen, amino, $C_1$–$C_4$alkylamino, phenylamino or di($C_1$–$C_4$alkyl)amino. Examples and preferred meanings are as given in U.S. Pat. No. 5,814,692, column 6, line 9, until column 7, line 20; these passages are hereby incorporated by reference.

Halogen is typically chloro, bromo or iodo. Chloro is preferred.

Alkanoyl of up to 25 carbon atoms is a branched or unbranched radical, typically formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. Alkanoyl of 2 to 18, in particular of 2 to 12, e.g. of 2 to 6, carbon atoms is preferred. Acetyl is particularly preferred. Examples for alkanoyl or alkanoyloxy (oxygen-capped alkanoyl) as well as alkanoyl interrupted by O, S or $NR_{14}$, and preferred meanings are as given in U.S. Pat. No. 5,814,692, column 7, lines 31–48, and column 8, lines 14–38; these passages are hereby incorporated by reference.

Alkenoyl of 3 to 25 carbon atoms is a branched or unbranched radical, typically propenoyl, 2-butenoyl, 3-butenoyl, isobutenoyl. Alkenoyloxy is oxygen-capped alkenoyl. Examples and preferred meanings for alkenoyl(oxy) as well as alkenoyl interrupted by O, S or $NR_{14}$ are as given in U.S. Pat. No. 5,814,692, column 7, line 48, until column 8, line 13; these passages are hereby incorporated by reference.

Examples and preferred meanings for $C_6$–$C_9$cycloalkylcarbonyl or $C_6$–$C_9$cycloalkylcarbonyloxy, $C_1$–$C_{12}$alkyl-substituted benzoyl or benzoyloxy, $C_1$–$C_{25}$alkyl, $C_3$–$C_{25}$alkenyl, $C_3$–$C_{25}$alkenyloxy, $C_3$–$C_{25}$alkynyl such as propargyl (—$CH_2$—C≡CH), alkynyloxy (oxygen capped alkynyl), $C_2$–$C_{25}$alkyl interrupted by oxygen, sulphur or $NR_{14}$; $C_7$–$C_9$phenylalkyl which is unsubstituted or substituted or interrupted; phenylalkoxy such as benzyloxy; alkyl substituted phenyl or phenoxy; $C_5$–$C_8$cycloalkyl or cycloalkoxy which is unsubstituted or substituted by alkyl; $C_1$–$C_{25}$alkoxy or O, S or $NR_{14}$-interrupted $C_2$–$C_{25}$alkoxy; alkylthio; alkylamino or di($C_1$–$C_4$alkyl)amino; alkanoylamino; or divalent residues such as $C_1$–$C_4$alkyl substituted $C_5$–$C_{12}$cycloalkylene, interrupted $C_2$–$C_{18}$alkylene, $C_2$–$C_9$alkenylene, $C_2$–$C_{20}$alkylidene, phenylalkylidene, $C_5$–$C_8$cycloalkylidene, $C_7$–$C_8$bicycloalkylene, unsubstituted or alkyl substituted phenylene or naphthylene, or alkyl substituted cycloalkylidene are as given in U.S. Pat. No. 5,814,692, column 8, line 39, until column 12, line 22; these passages are hereby incorporated by reference.

One of the preferred meanings of $R_2$ and $R_4$ is, for example, $C_1$–$C_{18}$alkyl. A particularly preferred meaning of $R_4$ is $C_1$–$C_4$alkyl. One of $R_2$ and $R_4$ is preferably a branched radical; especially preferred are both $R_2$ and $R_4$ branched radicals.

A mono-, di- or tri-valent metal cation is preferably an alkali metal cation, alkaline earth metal cation or aluminum cation, typically $Na^+$, $K^+$, $Mg^{++}$, $Ca^{++}$ or $Al^{+++}$.

Preferred are compositions containing a compound of formula I, wherein $R_2$, $R_3$ and $R_5$, independently, are H, Cl, hydroxy, $C_1$–$C_{25}$alkyl, $C_7$–$C_9$phenylalkyl, unsubstituted or $C_1$–$C_4$alkyl-substituted phenyl; $C_1$–$C_{18}$alkoxy, $C_1$–$C_{25}$alkanoyloxy, $C_3$–$C_{25}$alkenoyloxy; and where $R_4$ is Cl, hydroxy, $C_1$–$C_{25}$alkyl, $C_7$–$C_9$phenylalkyl, unsubstituted or $C_1$–$C_4$alkyl-substituted phenyl; $C_1$–$C_{18}$alkoxy, $C_1$–$C_{25}$alkanoyloxy, $C_3$–$C_{25}$alkenoyloxy or is a group —$C_mH_{2m}$—$COR_{15}$, —O—$(C_vH_{2v})$—$COR'_{15}$, —O—$(CH_2)_q$—$OR_{32}$, —$OCH_2$—CH(OH)—$CH_2$—$R'_{15}$, —$OCH_2$—CH(OH)—$CH_2$—$OR_{32}$, or where $R_3$, $R_5$ and $R_6$ are H, $R_4$ may be a residue of formula III, or where $R_8$ or $R_{10}$ are other than H, $R_4$ may also be hydrogen;

$R_6$ is H, $R_7$ and $R_9$ are each independently of one another hydrogen; halogen; $C_1$–$C_{25}$alkyl; $C_2$–$C_{25}$alkyl which is interrupted by oxygen, sulfur or

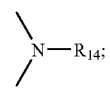

$C_3$–$C_{25}$-alkenyl; $C_3$–$C_{25}$alkynyl; $C_7$–$C_9$phenylalkyl; unsubstituted or $C_1$–$C_4$alkyl-substituted phenyl; unsubstituted or $C_1$–$C_4$alkyl-substituted $C_5$–$C_8$cycloalkyl;

$R_8$, $R_{10}$ and $R_{11}$ independently are H, halogen, hydroxy, $C_1$–$C_{25}$alkyl, O interrupted $C_2$–$C_{25}$alkyl; $C_1$–$C_{25}$alkoxy, O interrupted $C_2$–$C_{25}$alkoxy, $C_3$–$C_{25}$alkenyl, $C_3$–$C_{25}$alkenyloxy, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl substituted phenoxy; unsubstituted or $C_1$–$C_4$alkyl substituted $C_5$–$C_8$cycloalkyl; unsubstituted or $C_1$–$C_4$alkyl substituted $C_5$–$C_8$cycloalkoxy; $C_1$–$C_4$alkylamino, di($C_1$–$C_4$alkyl)amino, $C_1$–$C_{25}$alkanoyl; $C_1$–$C_{25}$alkanoyloxy; $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl substituted benzoyloxy;

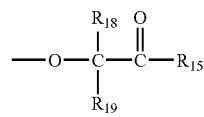

or

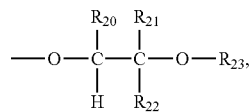

or where in formula II $R_7$ and $R_8$ or $R_8$ and $R_{11}$ together with the carbon atoms, they are bonded to, form a phenyl ring;

$R_{15}$ and $R'_{15}$ independently are $C_1$–$C_{18}$alkoxy; $C_3$–$C_{20}$alkoxy interrupted by O and/or substituted by a radical selected from OH, phenoxy, $C_7$–$C_{15}$alkylphenoxy, $C_7$–$C_{15}$alkoxyphenoxy; or are $C_5$–$C_{12}$cycloalkoxy; $C_7$–$C_{17}$phenylalkoxy; phenoxy; or —$NR_{23}R_{24}$; or a group of formula IIIa or IIIb;

$R_{16}$ and $R_{17}$ independently are H, $CF_3$, $C_1$–$C_{12}$alkyl or phenyl; or $R_{16}$ and $R_{17}$ together with the bonding carbon atom form an unsubstituted or 1–3 $C_1$–$C_4$alkyl-substituted $C_5$–$C_8$cycloalkylidene ring;

$R_{18}$ and $R_{19}$ independently are H, $C_1$–$C_4$alkyl or phenyl;

$R_{20}$ is H or $C_1$–$C_4$alkyl;

$R_{21}$ is H, unsubstituted or $C_1$–$C_4$alkyl substituted phenyl; $C_1$–$C_{25}$alkyl, unsubstituted or on the phenyl ring 1–3 $C_1$–$C_4$alkyl-substituted $C_7$–$C_9$phenylalkyl;

$R_{22}$ is H or $C_1$–$C_4$alkyl;

$R_{23}$ is H, $C_1$–$C_{25}$alkanoyl, $C_3$–$C_{25}$alkenoyl; di($C_1$–$C_6$alkyl)phosphonate-substituted $C_2$–$C_{25}$alkanoyl; $C_6$–$C_9$cycloalkylcarbonyl, thenoyl, furoyl, benzoyl or $C_1$–$C_{12}$alkyl-substituted benzoyl;

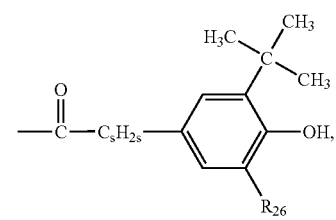

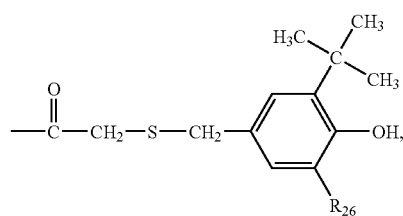

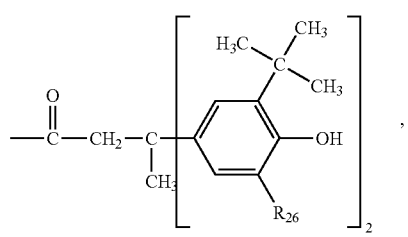

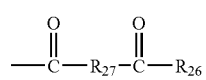

or

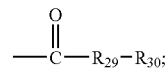

$R_{24}$ and $R_{25}$ independently are H or $C_1$–$C_{18}$alkyl;

$R_{26}$ is H or $C_1$–$C_8$alkyl; $R_{27}$ is a direct bond, $C_1$–$C_{18}$alkylen, $C_2$–$C_{18}$alkenylen, $C_7$–$C_{20}$phenylalkyliden, $C_5$–$C_8$cycloalkylen, unsubstituted or $C_1$–$C_4$alkyl-substituted

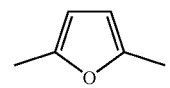

or

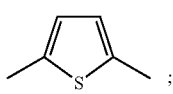

$R_{28}$ $C_1$–$C_{18}$alkoxy or

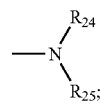

$R_{29}$ is O or —NH—;
$R_{30}$ is $C_1$–$C_{18}$alkyl or phenyl;
M a metal cation of the valency r;
X a direct bond, O, S or —$NR_{31}$—;
n is 1 or 2;
m is a number from the range 1–8;
q 1, 2, 3, 4, 5 or 6;
r 1, 2 or 3; and
s is 0, 1 or 2.

More preferred for use according to present invention is a compound of the formula IV

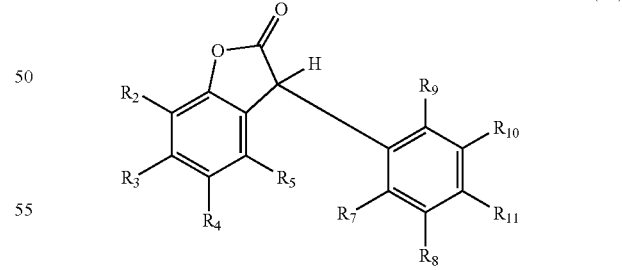

wherein
$R_2$ is H or $C_1$–$C_{20}$alkyl;
$R_3$ is H or $C_1$–$C_{18}$alkyl;
$R_4$ is $C_1$–$C_8$alkyl, H, $C_1$–$C_6$alkoxy or a group —$C_mH_{2m}$—$COR_{15}$; —O—($C_vH_{2v}$)—$COR_{15}$, —O—$(CH_2)_q$—$OR_{32}$; —$OCH_2$—CH(OH)—$CH_2$—$R_{15}$; —$OCH_2$—CH(OH)—$CH_2$—$OR_{32}$; or a group of the formula III;
$R_5$ is H or $C_1$–$C_{18}$alkyl;

$R_7$ and $R_9$ are each independently of one another hydrogen; halogen; $C_1$–$C_{25}$alkyl; $C_3$–$C_{25}$alkenyl $C_3$–$C_{25}$alkynyl; $C_7$–$C_9$phenylalkyl; unsubstituted or $C_1$–$C_4$alkyl-substituted phenyl; unsubstituted or $C_1$–$C_4$alkyl-substituted $C_5$–$C_8$cycloalkyl;

$R_8$, $R_{10}$ and $R_{11}$ independently are H, OH, chloro, $C_1$–$C_{18}$alkyl, $C_1$–$C_{18}$alkoxy, di($C_1$–$C_4$alkyl)amino, $C_7$–$C_9$phenylalkyl; unsubstituted or $C_1$–$C_4$alkyl-substituted phenyl; unsubstituted or $C_1$–$C_4$alkyl-substituted $C_5$–$C_8$cycloalkyl; $C_2$–$C_{18}$alkanoyloxy, $C_3$–$C_{18}$alkoxycarbonylalkoxy or

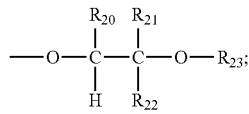

especially wherein at least 2 of the residues $R_7$, $R_8$, $R_9$, $R_{10}$, $R_{11}$ are H;

$R_{15}$ is $C_1$–$C_{18}$alkoxy; $C_3$–$C_{20}$alkoxy interrupted by O; or are cyclohexyloxy; $C_7$–$C_{17}$phenylalkoxy; phenoxy; or a group of formula IIIa or IIIb;

$R_{16}$ and $R_{17}$ independently are H, $C_1$–$C_{12}$alkyl or phenyl; or $R_{16}$ and $R_{17}$ together with the bonding carbon atom form a $C_5$–$C_8$cycloalkylidene ring;

$R_{20}$, $R_{21}$ and $R_{22}$ independently are H or $C_1$–$C_4$alkyl;

$R_{23}$ is H, $C_2$–$C_{16}$alkanoyl or a group

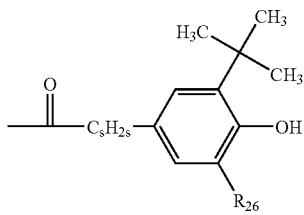

$R_{26}$ is $C_1$–$C_4$alkyl;

$R_{32}$ is $C_1$–$C_{18}$alkanoyl; $C_1$–$C_8$alkanoyl substituted by phenyl or $C_7$–$C_{15}$alkylphenyl; $C_3$–$C_{18}$alkenoyl; cyclohexylcarbonyl; or naphthylcarbonyl;

L is a divalent group —O—; Q—$C_2$–$C_{12}$alkylene-Q; —O—CH$_2$—CH(OH)—CH$_2$—O—;
—Q—$C_2$–$C_{12}$alkylene-Q—CO—$C_v$H$_{2v}$—O—;
—O—$C_2$–$C_{12}$alkylene-O—CH$_2$—CH(OH)—CH$_2$—O—;

Q is oxygen;
Z is $C_2$–$C_{12}$alkylene;
k is 1;
m is 1, 2, 3, 4, 5 or 6;
v is 1 or 2; and
s is 0, 1 or 2. Groups of formulae III, IIIa and IIIb are as defined above for formula I.

$R_4$ is preferably not H, most preferably not H and not OH. Especially preferred is a compound wherein $R_4$ is $C_1$–$C_6$alkyl, especially tertiary $C_4$–$C_6$alkyl, or a group —$C_mH_{2m}$—COR$_{15}$, —O—($C_vH_{2v}$)—COR$_{15}$, —O—(CH$_2$)$_q$—OR$_{32}$, —OCH$_2$—CH(OH)—CH$_2$—R$_{15}$, —OCH$_2$—CH(OH)—CH$_2$—OR$_{32}$, or a group of the formula III, especially —$C_mH_{2m}$—COR$_{15}$ or a group of the formula III.

Most preferred for use according to present invention is a compound of the formula IV wherein
$R_2$ is $C_1$–$C_{20}$alkyl;
$R_3$ is H or $C_1$–$C_{18}$alkyl;
$R_4$ is $C_1$–$C_6$alkyl, $C_1$–$C_6$alkoxy or a group —$C_mH_{2m}$—COR$_{15}$ or a group of the formula III;
$R_5$ is H or $C_1$–$C_{18}$alkyl;
$R_7$ and $R_9$ independently are H, chloro, $C_1$–$C_{18}$alkyl;
$R_8$, $R_{10}$ and $R_{11}$ independently are H, OH, chloro, $C_1$–$C_{18}$alkyl, $C_1$–$C_{18}$alkoxy, di($C_1$–$C_4$alkyl)amino, phenyl, $C_2$–$C_{18}$alkanoyloxy or

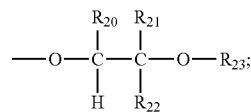

$R_{15}$ is $C_1$–$C_{18}$alkoxy or a group of the formula IIIa;
$R_{20}$, $R_{21}$ and $R_{22}$ are H;
$R_{23}$ is H, $C_2$–$C_{18}$alkanoyl or a group

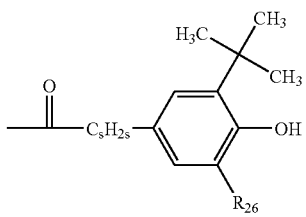

$R_{26}$ is $C_1$–$C_4$alkyl;
Q is oxygen;
Z is $C_2$–$C_{12}$alkylene;
k is 1;
m is 1, 2, 3, 4, 5 or 6 and
s is 0, 1 or 2.

Of special interest are those compounds of formula IV wherein $R_7$ is H and $R_9$ is H or methyl.

More interesting is a process where in the compound of formula I, if n=1, $R_1$ is phenyl which is unsubstituted or substituted in para-position by $C_1$–$C_{18}$alkylthio or di($C_1$–$C_4$-alkyl)amino; mono- to penta-substituted alkylphenyl containing together a total of at most 18 carbon atoms in the 1 to 5 alkyl substituents; naphthyl, biphenyl, terphenyl, phenanthryl, anthryl, fluorenyl, carbazolyl, thienyl, pyrrolyl, phenothiazinyl or 5,6,7,8-tetrahydronaphthyl which are unsubstituted or substituted by $C_1$–$C_4$-alkyl, $C_1$–$C_4$alkoxy, $C_1$–$C_4$alkylthio, hydroxy or amino.

Also preferred compositions contain compounds of the formula I wherein the bonding atom in $R_2$ is a secondary or tertiary carbon atom, especially wherein $R_2$ is secondary $C_6$–$C_{22}$ alkyl or tertiary $C_4$–$C_{22}$alkyl or phenyl or substituted phenyl or alkyl or alkoxy interrupted by COO; $R_4$ is secondary $C_6$–$C_{22}$ alkyl or tertiary $C_4$–$C_{22}$alkyl or a group of formula III or alkyl or alkoxy interrupted by COO; and $R_{11}$ is H or methyl or phenyl or alkyl or alkoxy interrupted by COO. Of special technical interest are compounds whose residues $R_2$, $R_4$ or $R_{11}$ contain an ester group.

Especially preferred are compounds of the formula IV wherein
$R_2$ is H or $C_1$–$C_{20}$alkyl;
$R_3$ is H or $C_1$–$C_{18}$alkyl;
$R_4$ is $C_1$–$C_6$alkyl, —(CH$_2$)$_p$—COR$_{15}$ or —C(CH$_3$)$_2$—(CH$_2$)$_p$—COR$_{15}$;
$R_5$ is H or $C_1$–$C_{18}$alkyl;
$R_7$, $R_8$, $R_9$, $R_{10}$ and $R_{11}$ independently are H, $C_1$–$C_{18}$alkyl, $C_1$–$C_{18}$alkoxy or

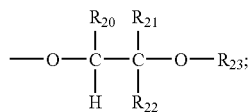

especially wherein at least 2 of the residues $R_7$, $R_8$, $R_9$, $R_{10}$, $R_{11}$ are H;

$R_{15}$ is $C_1$–$C_{18}$alkoxy;

$R_{20}$, $R_{21}$ and $R_{22}$ are H; and p is 2 or 3.

Compounds of the formula I or IV can be obtained according to methods known in the art, e.g. as described in U.S. Pat. No. 5,814,692 or publications cited therein, or, like compounds of formula V and VI, in analogy to those methods. Some compounds of the formula I are commercially available.

Lactones of present formula I are preferably used to trap the oxidised form of a developer having the following general structure:

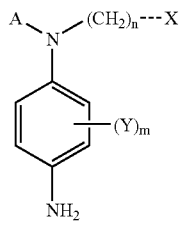

where $A=C_1$–$C_6$-alkyl;

n=1–6;

X=Hydrogen, hydroxy, $C_1$–$C_8$-alkoxy, $COR_{15}$, $NHSO_2R_{30}$, where $R_{15}$ and $R_{30}$ are as defined for formulae I or IV;

$Y=C_1$–$C_8$alkyl, $C_1$–$C_8$alkoxy, halogen; m=0–4.

In the above structure the preferred substituents are A=—$CH_2CH_3$ and n=2, X=hydrogen or —$NHSO_2CH_3$ or —OH or —$OCH_3$, Y=hydrogen or —$CH_3$ and m=1.

Examples of these are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-hydroxyethylaniline, 3-methyl-4-amino-N-ethyl-N-α-methanesulphonamidoethylaniline, 3-methyl-4-amino-N-ethyl-N-α-methoxyethyl-aniline, 3-α-methanesulphonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α'-(α"-methoxyethoxy)ethoxy]ethyl-3-methyl-4-aminoaniline, N-ethyl-N-α-(α'-methoxyethoxy)ethyl-3-methyl-4-aminoaniline, and also the salts of such compounds, for example sulphates, hydrochlorides or toluenesulphonates.

The photographic materials according to this invention comprise a support bearing at least one layer of a light-sensitive silver halide emulsion.

Examples of colour photographic materials according to this invention are colour negative films, colour reversal films, colour positive films, colour photographic paper, colour reversal photographic paper, colour-sensitive materials for the dye diffusion transfer process or the silver dye bleach process.

Of especial interest is a colour photographic recording material comprising, on a base, at least one blue-sensitive silver halide emulsion layer containing at least one yellow dye providing compound, at least one green-sensitive silver halide emulsion layer containing at least one magenta dye providing compound, at least one red-sensitive silver halide emulsion layer containing at least one cyan dye providing compound, and customary (non light sensitive) top layer(s) and interlayers separating the light-sensitive layers. The layers of the colour photographic material can be arranged in various orders as is well known in the art.

The compound of the formula I or IV can be contained in any of the layers of the photographic material, i.e. in any of the light sensitive silver halide emulsion layers or in a non light sensitive layer. For use as a Dox scavenger, the compound of the formula I is preferably contained in one or more non light sensitive layers. In this case, the light sensitive layers may contain a lower concentration of the compound of the formula I or none.

Compounds of formula I are preferably incorporated in an interlayer adjacent to the green-sensitive layer containing a magenta coupler. Preferred colour photographic materials within this invention are those wherein the magenta coupler is of the pyrazolo-azole type, e.g. as disclosed in U.S. Pat. No. 5,538,840, column 49, line 51, until column 69, line 27, and publications cited therein; this section of U.S. Pat. No. 5,538,840 is hereby incorporated by reference. Also preferred is a colour photographic material, wherein the silver halide emulsion contains at least 95 mol-% AgCl.

In general, the compounds of the formula I or IV are contained in the photographic material in an amount from 10 to 1000 mg/m², especially from 30 to 500 mg/m².

The lactones of formula I or IV can be milled with polymers (e.g. PVS, polyester, polyvinyl alcohol etc.) and placed in a layer thus preventing their migration to adjacent layers. Also, the benzofuranones containing a suitable functional group (e.g. ester, hydroxy) can be reacted with a polymer, e.g. a polyvinyl alcohol or polyester, in order to attach them chemically. This form will reduce their migrating tendency.

Typical bases for the photographic material include polymeric films and paper (including polymer-coated paper). Details regarding supports and other layers of colour photographic recording materials can be found in *Research Disclosure*, Item 36544, September 1994.

Essential constituents of the photographic emulsion layers are binders, silver halide particles and colour couplers. Details regarding the constituents of the light sensitive layers and other (non light sensitive) layers such as top layers and interlayers separating the silver halide emulsion layers can be found in *Research Disclosure*, Item 38957, September 1996.

The invention therefore also pertains to a colour photographic material comprising a compound of the formula I or IV, and to the use of a compound of the formula I or IV as an additive in a colour photographic material.

Preferred compounds of the formula I or IV in the colour photographic material of the invention or the corresponding use are as described for the process of the invention.

Compounds of present invention are of special advantage when incorporated into photographic materials containing magenta couplers of the pyrazolotriazole class.

Examples for especially suitable yellow, magenta and cyan couplers to be used in combination with compounds of the present invention are as given in U.S. Pat. No. 5,538,840, column 33, line 3, until column 73, line 34, and publications cited therein. These passages of U.S. Pat. No. 5,538,840 are hereby incorporated by reference.

The compounds of the formula (I) which can be used in the context of this invention can be incorporated into the colour photographic recording material, on their own or together with the colour coupler and with or without further additives, by pre-dissolving them in high-boiling organic solvents. Preference is given to the use of solvents which boil at higher than 160° C. Typical examples of these solvents are the esters of phthalic acid, phosphonic acid, citric acid, benzoic acid or of fatty acids, and also alkylamides and phenols.

Further details on the structure of the colour photographic material of the invention, and the components or further additives which can be employed in the novel material, can be found, inter alia, in U.S. Pat. No. 5,538,840, column 27, line 25, to column 33, line 2; and further in U.S. Pat. No. 5,538,840 from column 74, line 18, to column 106, line 16; and in U.S. Pat. No. 5,780,625, column 12, line 6, until column 57, line 6, and the publications cited in these 2 references; these passages of U.S. Pat. No. 5,538,840 and U.S. Pat. No. 5,780,625 are hereby incorporated by reference. Other useful information, how compounds of the formula I can be used in photographic material, can be taken from EP-A-871066, page 10, line 10, until page 11, line 32, especially the references cited therein.

The photographic layers in the material of this invention may also include UV absorbers, which screen out the UV light and therefore protect the dyes, the couplers or other components against photodegradation. Benzofuran-2-ones compounds according to this invention may be contained in those layers where UV absorbers are present.

UV absorbers preferably to be used in the novel material or within the process of present invention include benzotriazoles, 2-hydroxybenzophenones, oxanilides, cyanoacrylates, salicyclic esters, acrylonitrile derivatives, thiazolines and 2-hydroxyphenyltriazines.

GB-A-2319523 describes from page 49, line 21, until page 73, line 2, further details of the colour photographic material, especially couplers (page 52, line 1, until page 56, line 22), UV absorbers (page 56, line 25, until page 68, line 1) and dark stablisers (page 68, line 2, until page 73, line 2). Preferred UV absorbers of the 2-hydroxyphenyltriazine class are also described in detail, for example, in U.S. Pat. No. 5,668,200, column 1, line 30, until column 7, line 55, and as specific examples from column 26, line 31, until column 32, last line, and, together with some advantageous UV absorbers of the benzotriazole class, in U.S. Pat. No. 5,300,414, column 2 to column 10, line 54. These sections of U.S. Pat. No. 5,668,200 and U.S. Pat. No. 5,300,414 are hereby incorporated by reference.

The compounds of formula I may be used in combination with any known Dox scavengers such as hydrazines, hydrazides, hydroquinones of e.g. formula HQ-1 or HQ-2; 6-hydroxychromanes of e.g. formula A-3 or hydroxylamines of e.g. formula A-4:

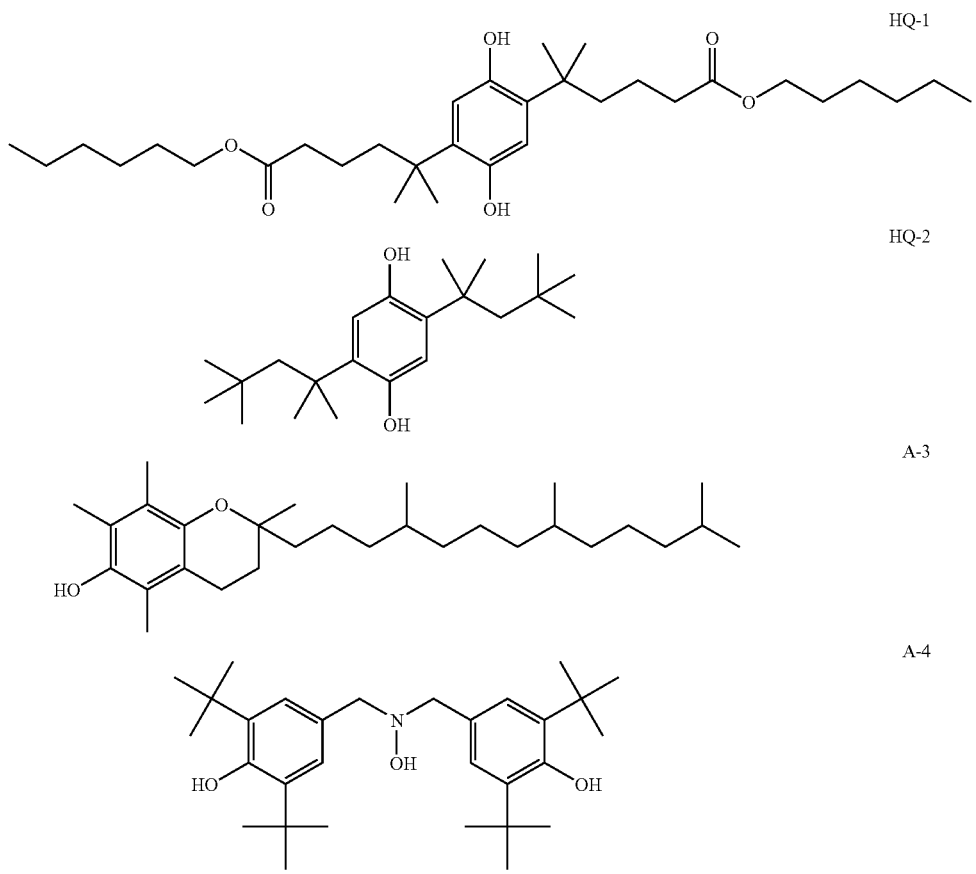

As silver halide emulsions it is possible to use customary silver chloride, silver bromide or silver iodide emulsions or mixtures thereof, such as silver chlorobromide and silver chloroiodide emulsions, in which the silver halides may have all known crystal forms. The use of silver chloride emulsions is accorded particular importance in the material of this novel process. The preparation of such emulsions and their sensitization are described in research disclosure, Item 307105, November 1989.

Besides their use in colour photographic materials, compounds of formula (I) or especially (IV) can also find utility in other recording materials, such as digital recording materials, for example, those for pressure-sensitive copying systems, microcapsule photocopier systems, heat-sensitive copier systems and ink-jet printing. By such materials are meant, for example, those described in Research Disclosure, Item 31429, 1990. Preparation and details of non-silver halide recording material of the invention especially for ink-jet printing can be taken from U.S. Pat. No. 5,686,633, column 6, line 55, until column 8, line 6, and U.S. Pat. No. 5,073,448, column 6, line 43, until column 11, line 57; these sections of U.S. Pat. No. 5,686,633 and U.S. Pat. No. 5,073,448 are hereby incorporated by reference. The inks according to the invention preferably contain 0.01–30% by weight, in particular 0.1–20% by weight, of a compound of the formula (I) or (IV).

Some of the compounds of the formula I are new compounds. Thus, the invention also pertains to a compound of the formula V or VI

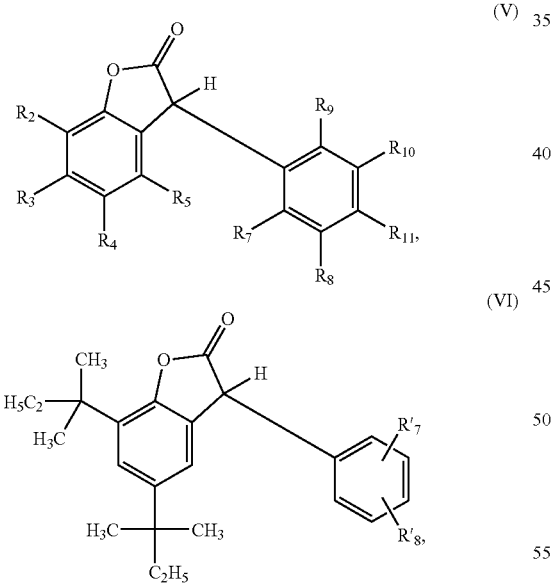

wherein $R_4$ is $-(CH_2)_s-COR'_{15}$ or $-CH(CH_3)-COR_{15}$ or $-C_tH_{2t}-COR_{15}$, wherein $C_tH_{2t}$ is a straight chain or branched alkylene moiety; or $R_4$ is $-O-(C_vH_{2v})-COR_{15}$; $-O-(CH_2)_q-OR_{32}$; $-OCH_2-CH(OH)-CH_2-R_{15}$; or $-OCH_2-CH(OH)-CH_2-OR_{32}$;

$R'_7$ is $C_1-C_4$alkyl and $R'_8$ is hydrogen or $C_1-C_4$alkyl;

$R_{15}$ is hydroxy;

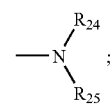

$C_1-C_{20}$alkoxy; $C_3-C_{20}$alkoxy interrupted by O and/or substituted by a radical selected from OH, phenoxy, $C_7-C_{15}$alkylphenoxy, $C_7-C_{15}$alkoxyphenoxy; or $R_{15}$ is $C_5-C_{12}$cycloalkoxy; $C_7-C_{17}$phenylalkoxy; phenoxy;

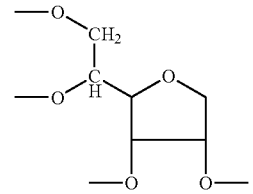

or a group of formula IIIa or IIIb;

$R'_{15}$ is $C_3-C_{20}$alkoxy interrupted by O and/or substituted by a radical selected from OH, phenoxy, $C_7-C_{15}$alkylphenoxy, $C_7-C_{15}$alkoxyphenoxy; or $R_{15}$ is $C_5-C_{12}$cycloalkoxy; $C_7-C_{17}$phenylalkoxy; phenoxy; or a group of formula IIIa or IIIb;

$R_{32}$ is $C_1-C_{18}$alkanoyl; $C_1-C_8$alkanoyl substituted by phenyl or $C_7-C_{15}$alkylphenyl; $C_3-C_{18}$alkenoyl; cyclohexylcarbonyl; or naphthylcarbonyl;

L is a linking group of valency (k+1) and

L is as a divalent group $-O-$; $Q-C_2-C_{12}$alkylene-Q; $-O-CH_2-CH(OH)-CH_2-O-$; $-Q-C_2-C_{12}$alkylene-Q$-CO-C_vH_{2v}-O-$; $-O-C_2-C_{12}$alkylene-O$-CH_2-CH(OH)-CH_2-O-$; Q-interrupted $Q-C_4-C_{12}$alkylene-Q; Q-phenylene-Q or Q-phenylene-D-phenylene-Q with D being $C_1-C_4$alkylene, O, S, SO or $SO_2$;

L as a trivalent group is Q-capped $C_3-C_{12}$alkanetriyl, a trivalent residue of a hexose or a hexitol, or a group $(-O-CH_2)_3C-CH_2OH$; $-Q-C_aH_{2a}-N(C_bH_{2b}-Q-)-C_cH_{2c}-Q-$; $-Q-C_3-C_{12}$alkanetriyl$(-Q-CO-C_vH_{2v}-O-)_2$; $-O-C_3-C_{12}$alkanetriyl$(-O-CH_2-CH(OH)-CH_2-O-)_2$; and L as a tetravalent group is a tetravalent residue of a hexose or a hexitol; $-Q-C_4-C_{12}$alkanetetryl$(-Q-CO-C_vH_{2v}-O-)_3$; $-O-C_4-C_{12}$alkanetetryl$(-O-CH_2-CH(OH)-CH_2-O-)_3$; Q-capped $C_4-C_{12}$alkanetetryl; a group

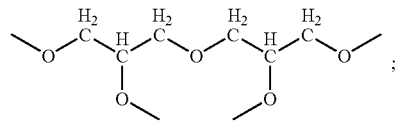

or a group v is 1, 2, 3, 4, 5, 6, 7 or 8, preferably 1 or 2;

Q is oxygen or $-NH-$,

Z is a linking group of valency (k+1) and is as a divalent group $C_2$–$C_{12}$alkylene, Q-interrupted $C_4$–$C_{12}$alkylene, phenylene or phenylene-D-phenylene with D being $C_1$–$C_4$alkylene, O, S, SO or $SO_2$;

Z as a trivalent group is $C_3$–$C_{12}$alkanetriyl, a trivalent residue of a hexose or a hexitol, a group (—$CH_2$)$_3$C—$CH_2OH$, or a group —$C_aH_{2a}$—N($C_bH_{2b}$—)—$C_cH_{2c}$—; and Z as a tetravalent group is a tetravalent residue of a hexose or a hexitol, $C_4$–$C_{12}$alkanetetryl, a group

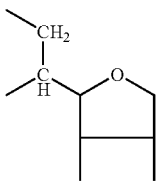

or a group

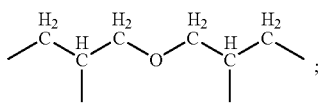;

a, b, c and k independently are 1, 2 or 3,
m is 0 or a number from the range 1–12, preferably 1–6;
s is 1 or 2;
and t is a number from the range 3–12, preferably 3–6;
and all other residues are as defined for formula I if n is 1.

Preferred compounds of the formula V are, within the limits given, as defined for formulae I or IV above. Also preferred are compounds of formula V, wherein $R_3$ and $R_5$ are H and $R_2$ is $C_1$–$C_8$alkyl, especially tert.butyl or tert.pentyl. Groups of formulae III, IIIa and IIIb are as defined above for formulae I or IV. Where $R_{15}$ or $R'_{15}$ contains a group of formula IIIa or IIIb (di-, tri- or tetrameric benzofuranones of formula V), those compounds having symmetrical linking moieties are preferred.

Preferred compounds of the formula VI are those wherein $R'_7$ is methyl or isopropyl and $R'_8$ is hydrogen or methyl.

Compounds of the formulae V and VI are also useful as stabilisers for organic material against degradation by light, oxygen and/or heat. Application of these compounds and methods of stabilising are generally as described in GB-A-2322861; examples for organic material which can be stabilized are listed, for example, in GB-A-2319523 from page 15, line 11, until page 20, line 25; possible costabilizers are as listed, for example in GB-A-2319523 from page 21, line 16, until page 32, bottom line. Examples for organic materials which can be stabilized as well as methods of stabilization are also listed in U.S. Pat. No. 5,668,200, from column 8, line 18, to column 11, line 25, and from column 18, line 29, to column 22, line 53, and additionally in column 25, lines 29–67; possible costabilizers and their dosage are as listed in U.S. Pat. No. 5,668,200, column 11, line 51, to column 18, line 28, and column 22, line 54, to column 25, line 28, and in column 26, lines 9–15; these passages of U.S. Pat. No. 5,668,200 are hereby incorporated by reference. Compounds of the formula V or VI are used for this application preferably in an amount of 0.0005 to 5%, especially 0.01 to 1%, based on the weight of the organic material to be stabilised. The invention also pertains to a composition comprising (a) an organic material which may be subject to degradation by light, oxygen and/or heat, and (b) as stabilizer against these harmful effects a compound of the formula V and/or VI. Most preferred organic materials to be stabilized are synthetic organic polymers and organic dyes, especially thermoplastic polymers such as polyolefin, photographic or materials or coating materials.

Examples for compounds of the formula I to be used within this invention are:

Compound 1[a]:

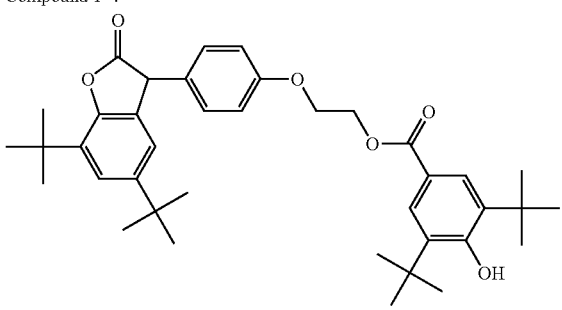

Compound 2:

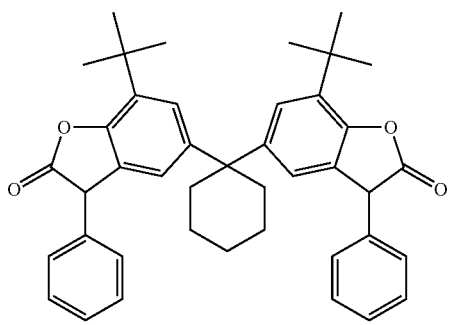

Compound 3[a]:

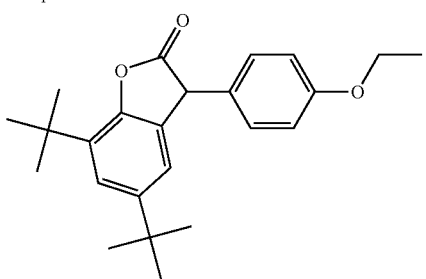

Compound 4[a]:

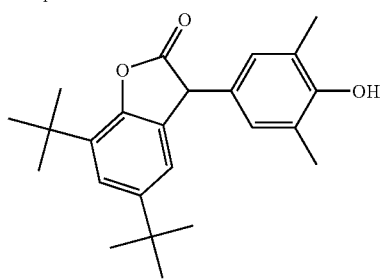

-continued
Compound 5:
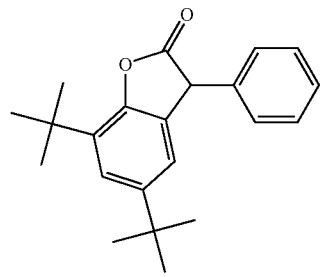
Compound 6<sup>a)</sup>:
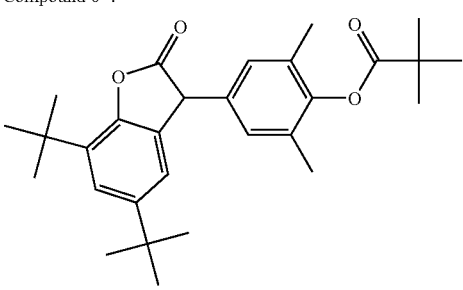
Compound 7<sup>a)</sup>:
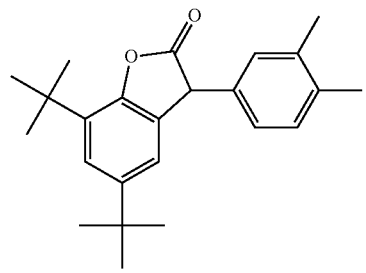
Compound 8:
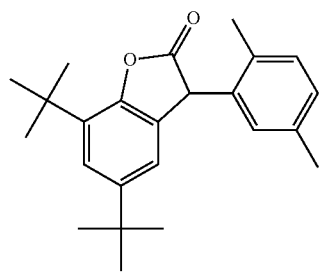
Compound 9<sup>a)</sup>:
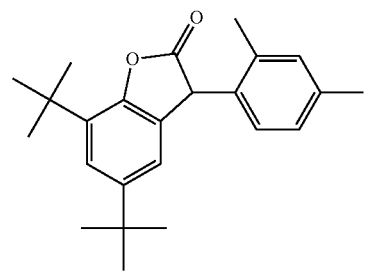
Compound 10<sup>a)</sup>:
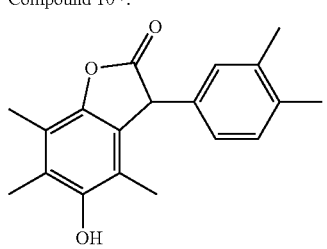
Compound 11<sup>a)</sup>:
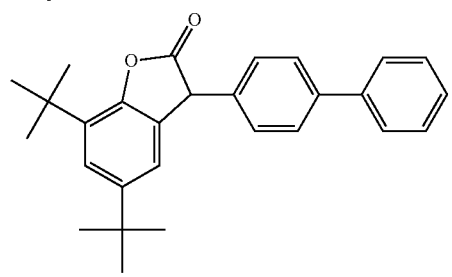
Compound 12<sup>a)</sup>:
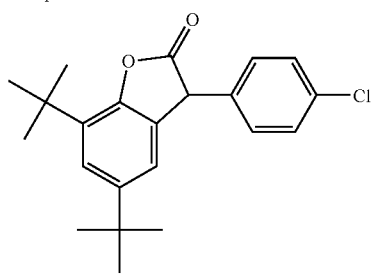
Compound 13<sup>a)</sup>:
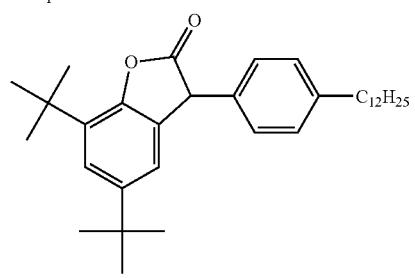
Compound 14<sup>a)</sup>:
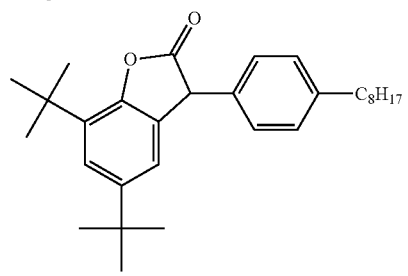

-continued
Compound 15<sup>a)</sup>:
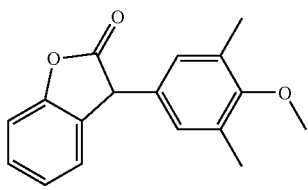
Compound 16<sup>a)</sup>:
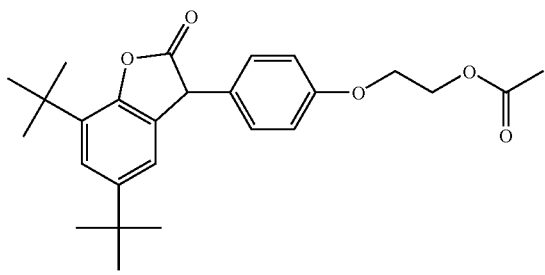
Compound 17<sup>a)</sup>:
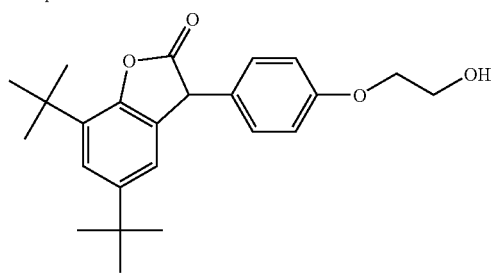
Compound 18<sup>a)</sup>:
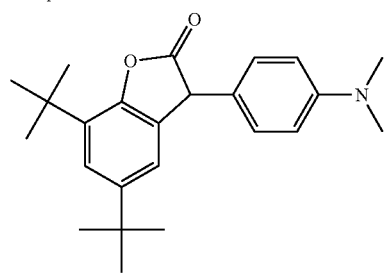
Compound 19:
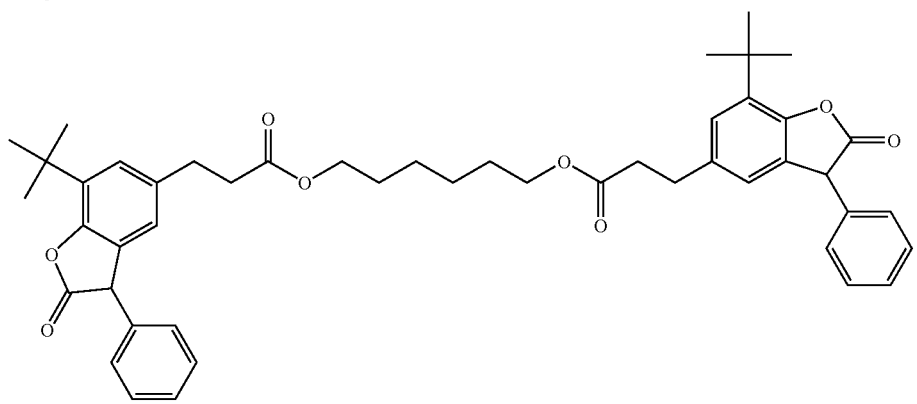
Compound 20:
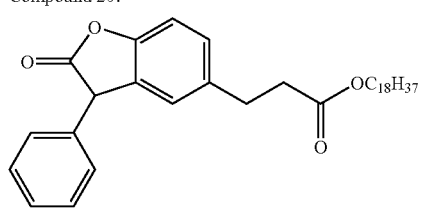
Compound 21<sup>a)</sup>:
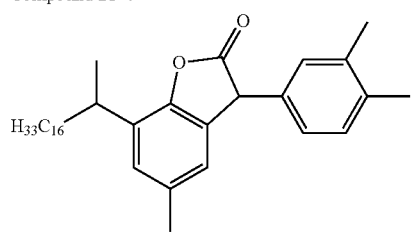
Compound 22:
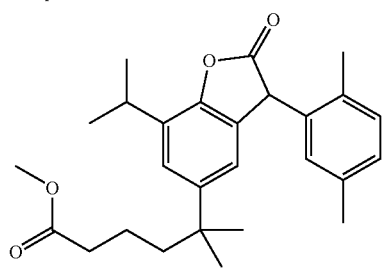
Compound 23<sup>a)</sup>:
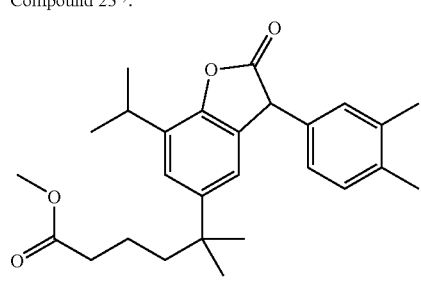

Compound 24:
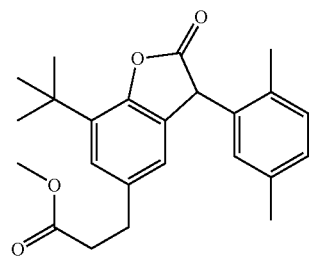
Compound 25[a)]:
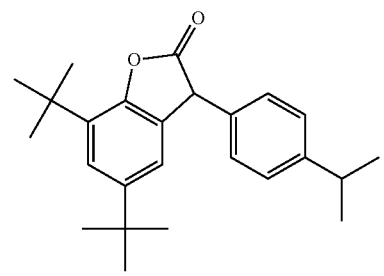
Compound 26[a)]:
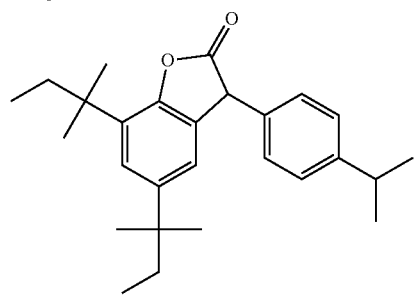
Compound 27[a)]:
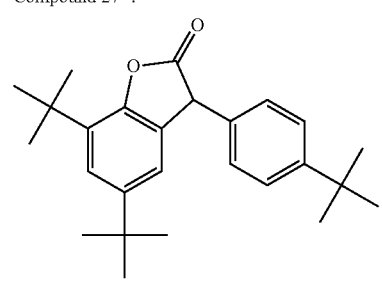
Compound 28:
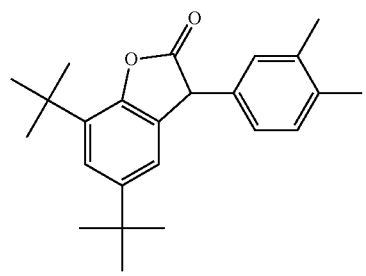
Compound 29:
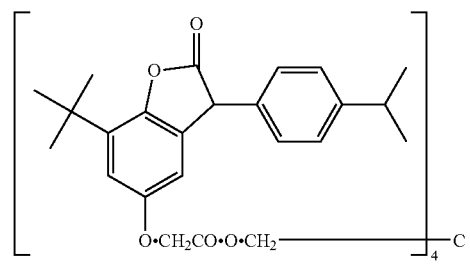
Compound 30:
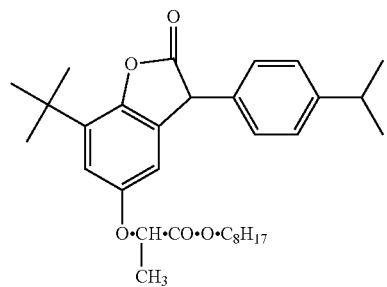
Compound 31:
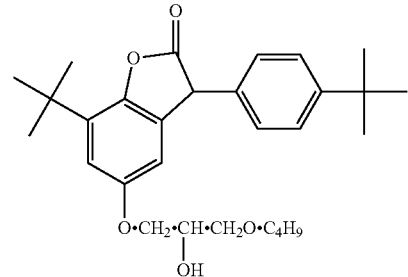
Compound 32:
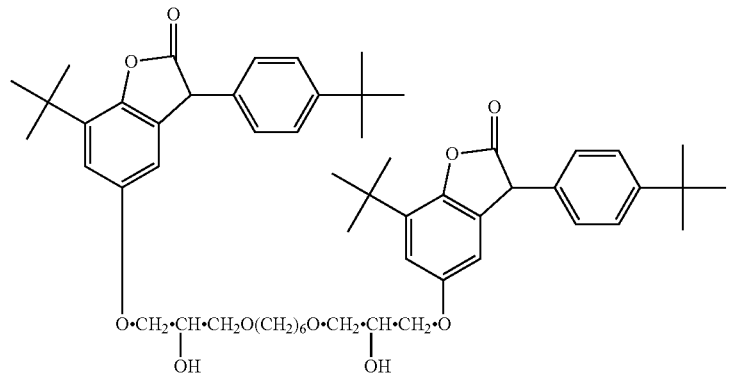

a) These products may additionally contain minor amounts of other structural isomers in accordance with the substitution at the phenyl ring in 3-position of the benzofuran-2-one. For example, compound 7 comprises the 2 isomers

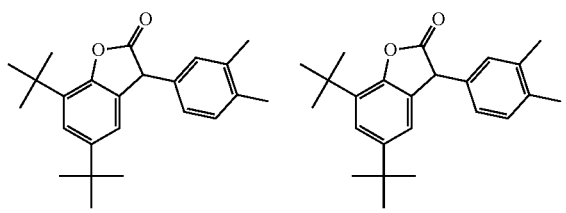

The synthetic methods used for the preparation of the benzofuran-2-ones shown above are described e.g. in U.S. Pat. Nos. 5,607,624 and 5,814,692. Examples for the synthesis of some new compounds among the above are given below from example 8 onwards.

Percentages given in the following examples are by weight if not otherwise indicated. Room temperature denotes a temperature in the range 20–25° C. Abbreviations:

TCP tricresyl phosphate;
RH relative humidity;
m.p. melting point or range;
NMR nuclear magnetic resonance of $^1H$;

Couplers: (M-3: see example 6 below)

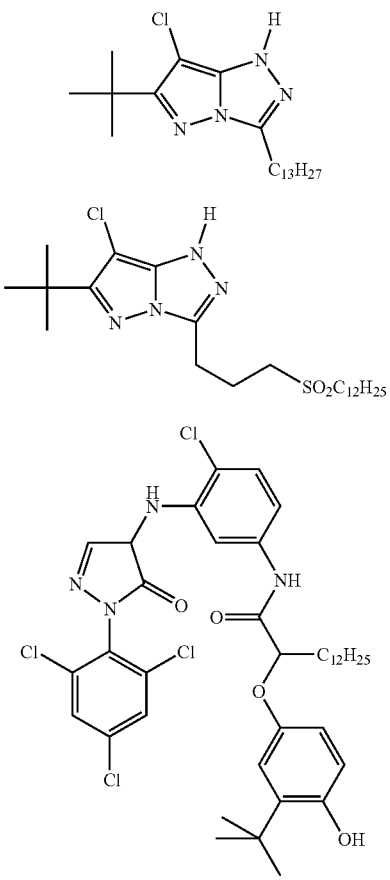

M-1

M-2

M-4

-continued

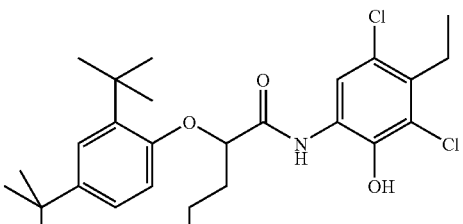

C-1

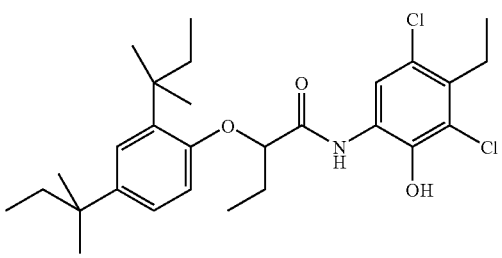

C-2

EXAMPLE 1

To evaluate compounds of this invention with respect to their ability as interlayer scavengers for oxidised developing agent, three layer photographic test elements are prepared by providing layers in the order indicated on a polyethylene-coated paper support:

Test Element 1 (Reference Sample)
(1) A layer containing:
  1800 mg.m$^{-2}$ of gelatin
  180 mg.m$^{-2}$ of dibutylphthalate
  2-sulphonate-4,8-diisobutyl-naphtalene, sodium salt surface active agent
(2) An interlayer containing:
  1800 mg.m$^{-2}$ of gelatin
  300 mg.m$^{-2}$ of tricresylphosphate
  2-sulphonate-4,8-diisobutyl-naphtalene, sodium salt surface active agent
(3) A photosensitive layer containing:
  260 mg.m$^{-2}$ (based on silver) of an unsensitized silver bromide emulsion
  1800 mg.m$^{-2}$ of gelatin
  300 mg.m$^{-2}$ of magenta-dye-forming coupler M-1
  300 mg.m$^{-2}$ of tricresylphosphate
  2-sulphonate-4,8-diisobutyl-naphtalene, sodium salt surface active agent
  2-hydroxy-4,6-dichloro-1,3,5-triazine, potassium salt hardener
  7-methyl-5-hydroxy-1,3,8-triazaindolizine antifoggant.

Test Element 2 (Check Sample)
(1) A layer containing:
  1800 mg.m$^{-2}$ of gelatin
  272 mg.m$^{-2}$ of cyan-dye-forming coupler C-1
  180 mg.m$^{-2}$ of dibutylphthalate
  2-sulphonate-4,8-diisobutyl-naphtalene, sodium salt surface active agent
(2) An interlayer having the same composition as the interlayer of test element 1

(3) A photosensitive layer having the same composition as the photosensitive layer of test element 1.

Test Elements 3–8

(1) A layer having the same composition as the first layer of test element 2

(2) An interlayer containing:

1800 mg.m$^{-2}$ of gelatin 0.056×10$^{-3}$ mol.m$^{-2}$ of oxidised developer scavenger as indicated in table 1 below 300 mg.m$^{-2}$ of tricresylphosphate 2-sulphonate-4,8-diisobutyl-naphtalene, sodium salt surface active agent (3) A photosensitive layer having the same composition as the photosensitive layer of test element 1.

The test elements are imagewise exposed through a step wedge with density increment 0.15 and thereafter subjected to the AGFA P-94 developing process.

Within test elements 2–9, cyan dye can only be formed by the wandering of the oxidised developer from the layer in which it is formed (i.e. the uppermost layer) to the bottom layer containing the cyan-dye-forming coupler. The ability of an interlayer scavenger to prevent oxidised developer from diffusing into the bottom layer can thus be assessed by determining the cyan density at any chosen exposure amount.

The cyan density at the exposure amount giving a magenta density of 2 is reported in table 1. The cyan density in the test element containing no cyan coupler in the bottom layer (test element 1) arises exclusively from the side absorption of the magenta dye in the red part of the visible spectrum.

TABLE 1

| Test element | Interlayer scavenger | Cyan density at a magenta density of 2 |
|---|---|---|
| 1 (reference) | none | 0.268 |
| 2 (check) | none | 0.400 |
| 3 | Compound 1 | 0.320 |
| 4 | Compound 2 | 0.278 |
| 5 | Compound 3 | 0.349 |
| 6 | Compound 4 | 0.313 |
| 7 | Compound 5 | 0.327 |
| 8 | Compound 6 | 0.319 |

Any cyan density inferior to that observed in sample 2 indicates scavenging of the oxidised developer. It is thus clear from the data in table 1 that compounds within the scope of this invention are very effective in preventing the oxidised developer from wandering and forming dye in the wrong layer.

EXAMPLE 2

Three layer photographic test elements are prepared by providing layers in the order indicated on a polyethylene-coated paper support:

Test Element 9 (Reference Sample)
    Same as test element 1 of example 1

Test Element 10 (Check Sample)
    (1) A layer containing:
    1800 mg.m$^{-2}$ of gelatin
    272 mg.m$^{-2}$ of cyan-dye-forming coupler C-2
    180 mg.m$^{-2}$ of dibutylphthalate
    2-sulphonate-4,8-diisobutyl-naphtalene, sodium salt surface active agent
    (2) An interlayer having the same composition as the interlayer of test element 9
    (3) A photosensitive layer having the same composition as the photosensitive layer of test element 9.

Test Elements 11–14
    (1) A layer having the same composition as the first layer of test element 10
    (2) An interlayer containing
    1800 mg.m$^{-2}$ of gelatin
    30 mg.m$^{-2}$ of oxidised developer scavenger as indicated in table 2 below
    300 mg.m$^{-2}$ of tricresylphosphate
    2-sulphonate-4,8-diisobutyl-naphtalene, sodium salt surface active agent
    (3) A photosensitive layer having the same composition as the photosensitive layer of test element 9.

The test elements are exposed and processed in the same manner as in example 1. The cyan density at the exposure amount giving a magenta density 2 is reported in table 2.

TABLE 2

| Test element | Interlayer scavenger | Cyan density at a magenta density of 2 |
|---|---|---|
| 9 (reference) | none | 0.264 |
| 10 (check) | none | 0.372 |
| 11 | Compound 7 | 0.284 |
| 12 | Compound 8 | 0.308 |
| 13 | Compound 9 | 0.300 |
| 14 | Compound 24 | 0.302 |

According to the data in table 2, the compounds of this invention used in the test elements 11–14 are very effective oxidised developer scavengers.

EXAMPLE 3

Three layer photographic test elements are prepared by providing layers in the order indicated on a polyethylene-coated paper support:

Test Element 15 (Check Sample)
    (1) A layer containing:
    1800 mg.m$^{-2}$ of gelatin
    272 mg.m$^{-2}$ of cyan-dye-forming coupler C-2
    180 mg.m$^{-2}$ of dibutylphthalate
    2-sulphonate-4,8-diisobutyl-naphtalene, sodium salt surface active agent
    (2) An interlayer containing:
    1800 mg.m$^{-2}$ of gelatin
    300 mg.m$^{-2}$ of tricresylphosphate
    2-sulphonate-4,8-diisobutyl-naphtalene, sodium salt surface active agent
    (3) A photosensitive layer containing:
    260 mg.m$^{-2}$ of an unsensitized silver bromide emulsion
    1800 mg.m$^{-2}$ of gelatin
    2-sulphonate-4,8-diisobutyl-naphtalene, sodium salt surface active agent 2-hydroxy-4,6-dichloro-1,3,5-triazine, sodium salt hardener 7-methyl-5-hydroxy-1,3,8-triazaindolizine antifoggant.

Test Elements 16–27

(1) A layer having the same composition as the first layer of test element 15

(2) An interlayer containing:

1800 mg.m$^{-2}$ of gelatin 30 mg.m$^{-2}$ of oxidised developer scavenger as indicated in table 3 below 300 mg.m$^{-2}$ of tricresylphosphate 2-sulphonate-4,8-diisobutyl-naphtalene, sodium salt surface active agent (3) A photosensitive layer having the same composition as the photosensitive layer of test element 15.

The test elements are given a stepped exposure and processed as in example 1.

Cyan dye formation within the above described test elements will again only result from the wandering of the oxidised developer from the photosensitive layer to the layer containing the cyan-dye-forming coupler. The ability of an interlayer scavenger to prevent oxidised developer from diffusing into the bottom layer can thus be assessed by measuring the cyan density at any given exposure.

As the above described samples contain no dye-forming coupler in the photosensitive layer, there is almost no consumption of the oxidised developer within the latter and the flux of oxidised developer through the interlayer towards the layer containing the cyan coupler is thus markedly increased as compared to the samples of examples 1 and 2.

In table 3, $(D_{cyan})_{1.35}$ is the cyan density at the exposure amount obtained behind the 1.35 density step of the step wedge. The smaller the $(D_{cyan})_{1.35}$ value, the more effective the scavenging of the oxidised developer.

TABLE 3

| Test element | Interlayer Scavenger | $(D_{cyan})_{1.35}$ |
| --- | --- | --- |
| 15 (check) | none | 0.405 |
| 16 | Compound 7 | 0.282 |
| 17 | Compound 10 | 0.250 |
| 18 | Compound 11 | 0.309 |
| 19 | Compound 12 | 0.292 |
| 20 | Compound 13 | 0.318 |
| 21 | Compound 14 | 0.324 |
| 22 | Compound 15 | 0.335 |
| 23 | Compound 16 | 0.300 |
| 24 | Compound 18 | 0.314 |
| 25 | Compound 19 | 0.335 |
| 26 | Compound 20 | 0.344 |
| 27 | Compound 21 | 0.314 |

From the data in table 3, it can be seen again that 3-aryl-3H-benzofuran-2-ones according to this invention exhibit outstanding scavenging ability, as evidenced by much smaller cyan density values in the test elements 16–27 as compared to the check sample.

EXAMPLE 4

Three layer photographic test elements are prepared by providing layers in the order indicated on a polyethylene-coated paper support:

Test Element 28 (Reference Sample)

(1) A layer containing:

1800 mg.m$^{-2}$ of gelatin 180 mg.m$^{-2}$ of dibutylphthalate 2-sulphonate-4,8-diisobutyl-naphtalene, sodium salt surface active agent (2) An interlayer containing:

1800 mg.m$^{-2}$ of gelatin 300 mg.m$^{-2}$ of tricresylphosphate 2-sulphonate-4,8-diisobutyl-naphtalene, sodium salt surface active agent (3) A photosensitive layer containing:

260 mg.m$^{-2}$ of an unsensitized silver bromide emulsion 1800 mg.m$^{-2}$ of gelatin 2-sulphonate-4,8-diisobutyl-naphtalene, sodium salt surface active agent 2-hydroxy-4,6-dichloro-1,3,5-triazine, sodium salt hardener 7-methyl-5-hydroxy-1,3,8-triazaindolizine antifoggant.

Test Element 29 (Check Sample)

Same as test element 15 of example 3 except that the cyan coupler used was C-1 instead of C-2.

Test Elements 30–33

(1) A layer having the same composition as the first layer of test element 29

(2) An interlayer containing:

1800 mg.m$^{-2}$ of gelatin

Oxidised developer scavenger as indicated in table 4 below 300 mg.m$^{-2}$ of tricresylphosphate 2-sulphonate-4,8-diisobutyl-naphtalene, sodium salt surface active agent (3) A photosensitive layer having the same composition as the photosensitive layer of test element 29.

The test elements are given a stepped exposure and processed as in example 1.

In table 4, $(D_{cyan})_{1.05}$ is the cyan density at the exposure amount obtained behind the 1.05 density step of the step wedge. The smaller the $(D_{cyan})_{1.05}$ value, the more effective the scavenging of the oxidised developer.

TABLE 4

| Test element | Interlayer Scavenger | Concentration | $(D_{cyan})_{1.05}$ |
| --- | --- | --- | --- |
| 28 (reference) | none | — | 0.080 |
| 29 (check) | none | — | 0.482 |
| 30 | Compound 7 | 30 mg · m$^{-2}$ | 0.390 |
| 31 | Compound 7 | 60 mg · m$^{-2}$ | 0.313 |
| 32 | Compound 7 | 90 mg · m$^{-2}$ | 0.202 |
| 33 | Compound 7 | 120 mg · m$^{-2}$ | 0.127 |

From the data in table 4, it can be seen that compound 7 according to this invention effectively prevents the formation of cyan dye, and that the Dox scavenging effect increases in proportion to the amount of added compound.

EXAMPLE 5

Three layer photographic test elements with a light sensitive layer on the bottom are similarly prepared, by providing layers in the order indicated onto a polyethylene coated paper support:

Test Element 34 (Reference Sample)
  (1) A photosensitive layer containing:
    260 mg.m$^{-2}$ (based on silver) of an unsensitized silver bromide emulsion
    1875 mg.m$^{-2}$ of gelatin
    250 mg.m$^{-2}$ of magenta-dye-forming coupler M-2
    250 mg.m$^{-2}$ of tricresylphosphate
    2-sulphonate-4,8-diisobutyl-naphtalene, sodium salt surface active agent
    7-methyl-5-hydroxy-1,3,8-triazaindolizine antifoggant.
  (2) An interlayer containing:
    1800 mg.m$^{-2}$ of gelatin
    300 mg.m$^{-2}$ of tricresylphosphate
    2-sulphonate-4,8-diisobutyl-naphtalene, sodium salt surface active agent
  (3) A layer containing:
    1800 mg.m$^{-2}$ of gelatin
    180 mg.m$^{-2}$ of dibutylphthalate
    2-sulphonate-4,8-diisobutyl-naphtalene, sodium salt surface active agent
    2-hydroxy-4,6-dichloro-1,3,5-triazine, potassium salt hardener Test Element 35 (Check Sample)
  (1) A photosensitive layer having the same composition as the photosensitive layer of test element 34
  (2) An interlayer having the same composition as the interlayer of test element 34
  (3) A layer containing:
    1800 mg.m$^{-2}$ of gelatin
    272 mg.m$^{-2}$ cyan-dye-forming coupler C-2
    180 mg.m$^{-2}$ of dibutylphthalate
    2-sulphonate-4,8-diisobutyl-naphtalene, sodium salt surface active agent
    2-hydroxy-4,6-dichloro-1,3,5-triazine, potassium salt hardener Test Elements 36–42
  (1) A photosensitive layer having the same composition as the photosensitive layer of test element 34
  (2) An interlayer containing:
    1800 mg.m$^{-2}$ of gelatin
    20 mg.m-2 of oxidised developer scavenger as indicated in table 5 below
    300 mg.m$^{-2}$ of tricresylphosphate
    2-sulphonate-4,8-diisobutyl-naphtalene, sodium salt surface active agent
  (3) A layer having the same composition as the top layer of test element 35.

The test elements are imagewise exposed through a step wedge with density increment 0.15 and thereafter subjected to the AGFA P-94 developing process.

Upon processing of the test elements, some oxidised developer migrates from the bottom layer to the top layer, thereby producing unwanted cyan dye.

The cyan density at the exposure amount giving a magenta density 2 is reported in table 5.

TABLE 5

| Test element | Interlayer scavenger | Cyan density at a magenta density of 2 |
|---|---|---|
| 34 (reference) | none | 0.290 |
| 35 (check) | none | 0.372 |
| 36 | Compound 3 | 0.324 |
| 37 | Compound 5 | 0.328 |
| 38 | Compound 7 | 0.324 |
| 39 | Compound 12 | 0.326 |
| 40 | Compound 16 | 0.331 |
| 41 | Compound 25 | 0.315 |
| 42 | Compound 27 | 0.328 |

EXAMPLE 6

Three layer photographic test elements are prepared by providing layers in the order indicated on a polyethylene-coated paper support:

Test Elements 46–73
  (1) A layer containing:
    1800 mg.m$^{-2}$ of gelatin
    an oxidised developer scavenger as indicated in table 6 below
    300 mg.m$^{-2}$ of tricresylphosphate
    2-sulphonate-4,8-diisobutyl-naphtalene, sodium salt surface active agent
  (2) A photosensitive layer containing:
    260 mg.m$^{-2}$ (based on silver) of an unsensitized silver bromide emulsion
    1800 mg.m$^{-2}$ of gelatin
    a magenta-dye-forming coupler as indicated in table 6
    a magenta dye light stabiliser as indicated in table 6
    tricresyl phosphate (TCP) as a high boiling solvent in the amount indicated in table 6
    2-sulphonate-4,8-diisobutyl-naphtalene, sodium salt surface active agent
    7-methyl-5-hydroxy-1,3,8-triazaindolizine antifoggant.
  (3) A layer containing:
    1800 mg.m$^{-2}$ of gelatin
    an oxidised developer scavenger as indicated in table 6
    300 mg.m$^{-2}$ of tricresylphosphate
    2-sulphonate-4,8-diisobutyl-naphtalene, sodium salt surface active agent
    2-hydroxy-4,6-dichloro-1,3,5-triazine, potassium salt hardener.

The test elements are imagewise exposed through a step wedge with density increment 0.30, and thereafter subjected to the AGFA P-94 developing process.

In order to evaluate them for light fastness, the stepped magenta images obtained in this manner are irradiated through an ultraviolet filter in an Atlas device equipped with a 3500 W Xenon lamp.

In a second experiment, magenta images obtained in the above described way are stored in the dark at 60° C., 95% relative humidity (RH) for 72 hours prior to light exposure in the Atlas device.

In all cases the light fastness of the magenta image is evaluated based on the percentage of the residual dye density after 30 kJ/cm$^2$ of light exposure (initial density=1). The results are given in table 6.

TABLE 6

| Test element | Middle layer components | | | Dox scavenger[1] | Residual dye after exposure (%) | |
|---|---|---|---|---|---|---|
| | Coupler[1] (mg · m$^{-2}$) | Stabiliser[1] (mg · m$^{-2}$) | Solv.[1] (mg · m$^{-2}$) | | no dark storage | 72 h dark storage |
| 46 control | M-1 (300) | S-1 (225) | TCP (300) | none | 75 | 75 |
| 47 comparison | M-1 (300) | S-1 (225) | TCP (300) | HQ-1 (80) | 74 | 60 |
| 48 comparison | M-1 (300) | S-1 (225) | TCP (300) | HQ-2 (80) | 71 | 45 |
| 49 invention | M-1 (300) | S-1 (225) | TCP (300) | Cpd. 7 (80) | 76 | 77 |
| 50 invention | M-1 (300) | S-1 (225) | TCP (300) | Cpd. 12 (80) | 77 | 74 |
| 51 invention | M-1 (300) | S-1 (225) | TCP (300) | Cpd. 21 (80) | 75 | 75 |
| 52 control | M-1 (300) | S-3 + S-4 (130 + 120) | TCP (300) | none | 68 | 60 |
| 53 comparison | M-1 (300) | S-3 + S-4 (130 + 120) | TCP (300) | HQ-1 (120) | 69 | 41 |
| 54 comparison | M-1 (300) | S-3 + S-4 (130 + 120) | TCP (300) | HQ-2 (120) | 65 | 12 |
| 55 invention | M-1 (300) | S-3 + S-4 (130 + 120) | TCP (300) | Cpd. 7 (120) | 71 | 56 |
| 56 control | M-2 (250) | S-3 + S-4 (100 + 100) | TCP (250) | none | 75 | 69 |
| 57 comparison | M-2 (250) | S-3 + S-4 (100 + 100) | TCP (250) | HQ-1 (120) | 72 | 37 |
| 58 comparison | M-2 (250) | S-3 + S-4 (100 + 100) | TCP (250) | HQ-2 (120) | 66 | 16 |
| 59 invention | M-2 (250) | S-3 + S-4 (100 + 100) | TCP (250) | Cpd. 7 (120) | 74 | 63 |
| 60 control | M-2 (250) | S-2 + S-4 (100 + 100) | TCP (250) | none | 71 | 66 |
| 61 comparison | M-2 (250) | S-2 + S-4 (100 + 100) | TCP (250) | HQ-1 (120) | 68 | 33 |
| 62 comparison | M-2 (250) | S-2 + S-4 (100 + 100) | TCP (250) | HQ-2 (120) | 61 | 22 |
| 63 invention | M-2 (250) | S-2 + S-4 (100 + 100) | TCP (250) | Cpd. 7 (120) | 70 | 64 |
| 64 control | M-2 (250) | S-2 + S-4 (200 + 200) | TCP (250) | none | 78 | 75 |
| 65 comparison | M-2 (250) | S-2 + S-4 (200 + 200) | TCP (250) | HQ-1 (120) | 75 | 45 |
| 66 comparison | M-2 (250) | S-2 + S-4 (200 + 200) | TCP (250) | HQ-2 (120) | 70 | 35 |
| 67 invention | M-2 (250) | S-2 + S-4 (200 + 200) | TCP (250) | Cpd. 7 (120) | 76 | 70 |
| 68 invention | M-2 (250) | S-2 + S-4 (200 + 200) | TCP (250) | Cpd. 8 (120) | 74 | 70 |
| 69 control | M-3 (300) | S-5 + S-6 (50 + 50) | TCP (600) | none | 91 | 98 |
| 70 comparison | M-3 (300) | S-5 + S-6 (50 + 50) | TCP (600) | HQ-1 (120) | 88 | 87 |
| 71 comparison | M-3 (300) | S-5 + S-6 (50 + 50) | TCP (600) | HQ-2 (120) | 87 | 68 |
| 72 invention | M-3 (300) | S-5 + S-6 (50 + 50) | TCP (600) | Cpd. 7 (120) | 91 | 97 |
| 73 invention | M-3 (300) | S-5 + S-6 (50 + 50) | TCP (600) | Cpd. 24 (120) | 90 | 96 |

[1]The coated amounts (mg · m$^{-2}$) are indicated in brackets. For the oxidised developer scavenger, the indicated amounts are for each of the two scavenger-containing layers.

Components used in test elements 46–73:
TCP=Tricresylphosphate
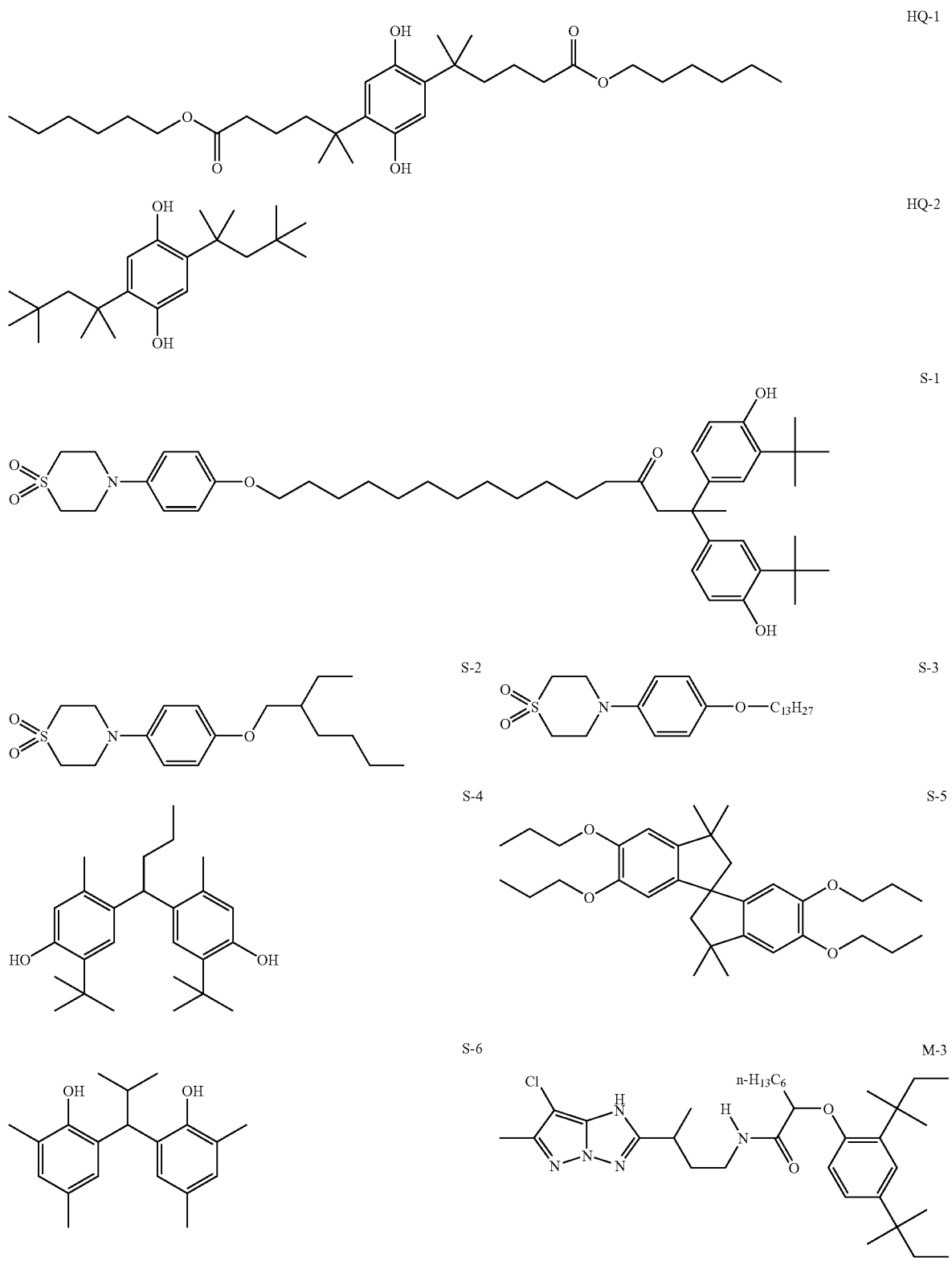
M-1: see above.

From the data in table 6, it can be seen that the oxidised developer scavengers according to this invention are not detrimental to the light stability of the magenta layer, whether the samples are subjected to a preliminary dark storage period at 60° C., 95% RH, or not. In contrast, the comparison hydroquinone scavengers HQ-1 and especially HQ-2 clearly impair the light fastness of the magenta image, especially in test elements that are left under a high temperature and humidity for 72 hours prior to exposure in the Atlas.

EXAMPLE 7

Test element 74 is prepared by providing on a polyethylene-coated paper support a light-sensitive silver halide layer containing:
- 260 mg.m$^{-2}$ (based on silver) of an unsensitized silver bromide emulsion
- 5150 mg.m$^{-2}$ of gelatin
- 305 mg.m$^{-2}$ of magenta-dye-forming compound M-1
- 305 mg.m$^{-2}$ of tricresylphosphate
- 2-sulphonate-4,8-diisobutyl-naphtalene, sodium salt surface active agent
- 2-hydroxy-4,6-dichloro-1,3,5-triazine, potassium salt hardener
- 7-methyl-5-hydroxy-1,3,8-triazaindolizine antifoggant Test elements 75 and 76 are prepared identically to test element 74, except that the emulsion layer additionally contains 30 mg.m$^{-2}$ and 75 mg.m$^{-2}$ of compound 7, respectively.

Test element 77 is prepared by providing on a polyethylene-coated paper support a light-sensitive silver halide layer containing:
- 520 mg.m$^{-2}$ (based on silver) of an unsensitized silver bromide emulsion
- 5150 mg.m$^{-2}$ of gelatin
- 417 mg.m$^{-2}$ of magenta-dye-forming compound M-4
- 208 mg.m$^{-2}$ of tricresylphosphate
- 2-sulphonate-4,8-diisobutyl-naphtalene, sodium salt surface active agent
- 2-hydroxy-4,6-dichloro-1,3,5-triazine, potassium salt hardener
- 7-methyl-5-hydroxy-1,3,8-triazaindolizine antifoggant Test element 78 is prepared identically to test element 77, except that the emulsion layer additionally contains 105 mg.m$^{-2}$ of compound 7.

The prepared test elements are imagewise exposed through a step wedge with density increment 0.30 and thereafter subjected to the AGFA P-94 developing process.

The stepped magenta images obtained in this manner are irradiated through an ultraviolet filter in an Atlas device equipped with a 3500 W Xenon lamp.

The light fastness of the magenta image is evaluated based on the percentage of the residual dye density after 15 kJ/cm$^2$ of light exposure (initial density=1). The results are given in table 7.

TABLE 7

| Test element | Benzofuranone | Residual dye after 15 kJ · cm$^{-2}$ of Atlas exposure (%) |
|---|---|---|
| 74 (control) | none | 31 |
| 75 | compound 7 (30 mg · m$^{-2}$) | 48 |
| 76 | compound 7 (75 mg · m$^{-2}$) | 77 |
| 77 (control) | none | 67 |
| 78 | compound 7 (105 mg · m$^{-2}$) | 75 |

As compared to a layer without added benzofuranone, magenta layers containing compound 7 are more stable to light. The benzofuranone derivatives according to this invention can therefore find utility as light stabilisers for photographic dyes, especially for those dyes that result from pyrazolone or pyrazolo-azole couplers.

Synthesis of New Compounds of Formula I

EXAMPLE 8

5,7-Di-tert-pentyl-3(4-isopropylphenyl)-3H-benzofuran-2-one (Compound No. 26)

a) 2,6-Di-tert-pentylphenol (161.4 g), glyoxylic acid (122.3 g of the 50% b.w. solution in water) and 1.3 g of p-toluene sulphonic acid are heated in 500 ml of ethylenechloride under nitrogen at reflux temperature in an apparatus designed for the removal of water. After 3.5 hours the reaction mixture is cooled to room temperature, washed 3 times with 25 ml water, dried over magnesium sulphite and evaporated under reduced pressure to give 214.3 g of: 5,7-di-tert-pentyl-3-hydroxy-3H-benzofuran-2-one as an orange coloured oil.

b) 29.6 g of the product obtained under (a) are heated together with cumane (150 ml) and an acid earth catalyst (Fulcat® 22 B, supplied by Laport, GB) under nitrogen to reflux. After 2 hours, the reaction mixture is filtered hot. Evaporation of the filtrate gives 35.1 g of raw product, which is subjected to chromatography on silica gel using hexane/ethyl acetate (4:1) as eluant. 26.7 g of the title product (compound No. 26) are obtained as an orange coloured oil. NMR (CDCl$_3$) 3-H: 5.29 ppm.

EXAMPLE 9

Preparation of 7-Isopropyl-5-(4-methoxycarbonyl-1,1-dimethylbutyl)-3,4-dimethylphenyl-3H-benzofuran-2-one (Compound No. 23)

a) 5-Methyl-5-(4-hydroxy-3-isopropyl phenyl)-hexanoic acid methyl ester (10.0 g), glyoxylic acid (6.4 g of the 50% solution in water) and p-toluene sulphonic acid (40 mg) are heated in 40 ml of ethylene chloride under nitrogen at reflux in an apparatus designed for the removal of water. After 5 hours the reaction mixture is cooled to room temperature, washed two times with 25 ml water, dried over magnesium sulphate and evaporated under reduced pressure to give 13 g of 7-isopropyl-5-(4-methoxycarbonyl-1,1-dimethylbutyl)-3-hydroxy-3H-benzofuran-2-one as a yellow oil.

b) 13 g of the above product (a), o-xylene (50 ml) are heated together with an acid earth catalyst (see example 8b) under nitrogen at reflux for 2.5 hours. The reaction mixture is filtered hot and the filtrate evaporated to give 16.6 g of a yellow oil. This is chromatographed over silica gel using hexane/ethylacetate 20:5 as eluant. 10.4 g of the mixture of the 2 isomers 7-isopropyl-5-(4-methoxycarbonyl-1,1-dimethylbutyl)-3,4-dimethylphenyl-3H-benzofuran-2-one and 7-isopropyl-5-(4-methoxycarbonyl-1,1-dimethylbutyl)-3-(2,3-dimethylphenyl)-3H-benzofuran-2-one as a slightly brown resin is obtained. NMR (CDCl$_3$) 3-H: 4.80 ppm.

EXAMPLE 10

Preparation of 7-Isopropyl-5-(4-methoxycarbonyl-1,1-dimethylbutyl)-3-(2,5-dimethylphenyl)-3H-benzofuran-2-one (Compound No. 22)

The product obtained in example 9a (14.35 g), p-xylene (50 ml) and an acid earth catalyst (see example 8b) are treated as described in example 9b to give 9.52 g of the title product (compound No. 22) as a slightly orange resin. NMR (CDCl$_3$) 3-H: 5.05 ppm.

EXAMPLE 11

Preparation of Compound No. 19 a) 3(7-.tert.-Butyl-2-oxo-3-phenyl-2,3-dihydro-benzofuran-5-yl)-propionic acid 122.3 g (0.55 mol) 3-(3-tert.-butyl-4-hydroxy-phenyl)-propionic acid (CAS Nr. 107551-67-7) and 92.1 g (0.61 mol) mandelic acid are melted together and then stirred under nitrogen at 200° C. during 4 h. The mixture is then cooled to room temperature, dissolved in toluene and chromatographed on silica gel with dichloromethane-ethyl acetate (3:1) to afford 103 g of the title compound as a pale yellow resin. $^1$H-NMR (100 MHz, CDCl$_3$): 7.4–6.9 m (7 ArH), 4.83 s (1H), 3.00–2.54 m (4H), 1.42 s (t-Bu).

b) 23.7 g (0.07 mol) of the product from example 11a, 4.2 g (0.035 mol) 1,6-hexanediol and 0.3 g p-toluene sulphonic acid are refluxed in 250 ml of xylene under Dean-Stark water separator during 6 h. The mixture is then cooled to room temperature, washed with water, dried with MgSO$_4$ and evaporated under vacuum. Chromatography of the residue on silica gel with dichloromethane-hexane (19:1) affords the 14.8 g of the compound No. 19 as a pale yellow oil. $^1$H-NMR (100 MHz, CDCl$_3$): 7.4–6.9 m (14 ArH), 4.82 s (2H), 4.08–3.96 m (4H), 2.98–2.51 m (8H), 1.61–1.26 m (4H), 1.42 s (t-Bu).

EXAMPLE 12

Preparation of 7-Tert.butyl-5-(2-methoxycarbonyl-ethyl)-3-(2,5-dimethylphenyl)-3H-benzofuran-2-one (Compound No. 24)

a) 3-(4-hydroxy-3-tert.butylphenyl) propionic acid methyl ester (10.0 g), glyoxylic acid (7.4 g of the 50% solution in water) and p-toluene sulphonic acid (40 mg) are heated in 40 ml ethylene chloride under nitrogen at reflux for 3 hours distilling off all water present and formed during the reaction. The reaction mixtures is washed with water, dried over magnesium sulphate and evaporated under reduced pressure to give 13.0 g of 7-tert.butyl-5-(2-methoxycarbonylethyl)-3-hydroxy-3H-benzofuran-2-one.

b) 13 g of the product from the above example 12a, 50 ml of p-xylene and an acid earth catalyst (see example 8b) are heated under nitrogen at reflux for 2.5 hours. The reaction mixture is filtered hot and the filtrate evaporated under reduced pressure to give 17.0 g of an orange oil. This is purified by column chromatography over 350 g silica gel using hexane/ethylacetate 4:1 as eluant to give the title product, which solidifies after two days. Recrystallization from hexane gives a colourless solid, mp 80°. NMR (CDCl$_3$) 3-H: 4.98 ppm.

EXAMPLE 13

Preparation of Compound No. 29 a) 2.40 g 2-(3-tert.Butyl-4-hydroxyphenoxy)-acetic acid methyl ester is heated 8 hrs. in 100 ml toluene at reflux with 0.34 g pentaerythritol in the presence of 0.1 g p-toluenesulphonic acid. The resulting methanol is distilled off using a Hickmann apparatus. The reaction mixture is cooled to room temperature, washed with water, dried over magnesium sulphate and evaporated under reduced pressure. The residue (2.24 g) is treated with glyoxylic acid (1.62 g of the 50% solution in water) and p.toluene sulphonic acid (0.1 g) and heated in 20 ml. ethylene chloride under nitrogen at reflux for 3.5 hrs., distilling off all water present and formed during the reaction. The reaction mixture is washed with water, dried over magnesium sulphate and evaporated under reduced pressure to give 2.80 g of compound X of the formula:

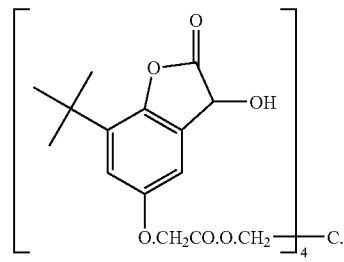

b) 2.8 g Of the above compound X, 25 ml. of cymene and an acid earth catalyst (see example 8b) are heated under nitrogen at reflux for 4 hrs. The reaction mixture is filtered hot and the filtrate evaporated under reduced pressure to give 3.50 g of impure product. This is purified by column chromatography over 160 g silica gel using hexane/ethyl acetate 4:1 as eluant to give purified compound No. 29 as a colourless resin.

EXAMPLE 14

Preparation of Compound No. 30 a) 3.50 g 2-(3-tert-Butyl-4-hydroxyphenoxy)-propionic acid octyl ester is heated 3 hrs. under nitrogen with glyoxylic acid (1.62 g of the 50% solution in water) and p-toluene sulphonic acid (0.1 g) in 20 ml ethylene chloride at reflux, distilling off the water present and formed during the reaction. The reaction mixture is washed with water, dried over magnesium sulphate and evaporated under reduced pressure to give 4.05 g of the below intermediate XII as a colourless oil:

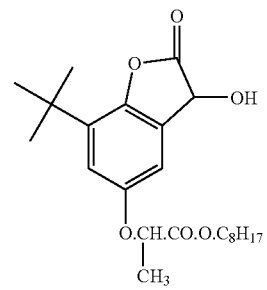

b) 4.05 g of the above intermediate XII, 25 ml. cymene and an acid catalyst (see example 8b) are heated under nitrogen at reflux for 3 hrs. The reaction mixture is filtered hot and the filtrate evaporated under reduced pressure to give 4.91 g of the title product XIII. This is purified by column chromatography using 150 g silica gel and hexane/ethyl acetate 4:1 as eluant to give purified compound No. 30 as a colourless oil.

EXAMPLE 15

Preparation of Compound No. 31 a) 3.00 g 1-Butoxy-2-hydroxy-3-(3-tert.butyl-4-hydroxyphenoxy)-propane is treated with glyoxylic acid (1.62 g of a 50% solution in water) and p-toluene sulphonic acid (0.1 g) and heated in 20 ml ethylene chloride under nitrogen at reflux for 2.5 hrs., distilling off all the water present and formed during the reaction. The reaction mixture is washed with water, dried over magnesium sulphate and evaporated under reduced pressure to give 3.62 g of crude intermediate XIV:

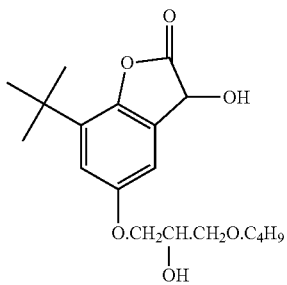

b) This was heated under nitrogen with an acid catalyst (see example 8b) in 25 ml refluxing tert.butylbenzene for 2.5 hrs. The reaction mixture is filtered hot and the filtrate evaporated under reduced pressure. The residue is purified by column chromatography over 150 g silica gel using hexane/ethylacetate 4:1 as eluant to give compound No. 31 as a colourless oil.

EXAMPLE 16

Preparation of Compound No. 32

Proceeding as in example 15, but using 2.92 g of compound XVI of formula

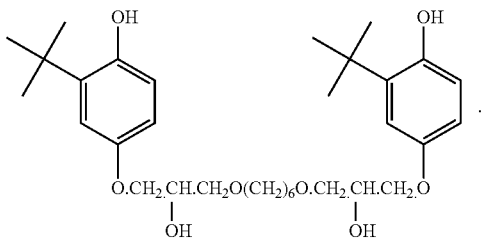

in step (a) instead of 1-butoxy-2-hydroxy-3-(3-tert.butyl-4-hydroxyphenoxy)-propane one obtains compounds No. 32 as a slightly yellow resin.

What is claimed is:

1. A process for preventing the migration of oxidised developer in a colour photographic material from a light sensitive silver halide emulsion layer in which it has been formed into another silver halide emulsion layer containing colour couplers comprising the steps of:

incorporating a compound of the formula I

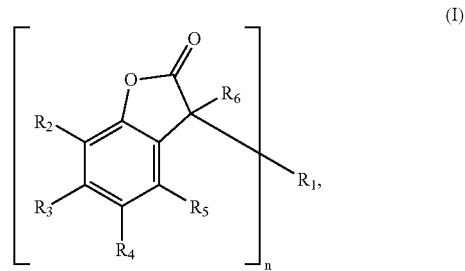

wherein, if n=1, $R_1$ is a cyclic residue selected from naphthyl, phenanthryl, anthryl, 5,6,7,8-tetrahydro-2-naphthyl, 5,6,7,8-tetrahydro-1-naphthyl, thienyl, benzo[b]thienyl, naphtho[2,3-b]thienyl, thianthrenyl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by $C_1$–$C_4$alkyl, $C_1$–$C_4$alkoxy, $C_1$–$C_4$alkylthio, hydroxy, halogen, amino, $C_1$–$C_4$alkylamino, phenylamino or di($C_1$–$C_4$-alkyl) amino; or $R_1$ is a radical of formula II

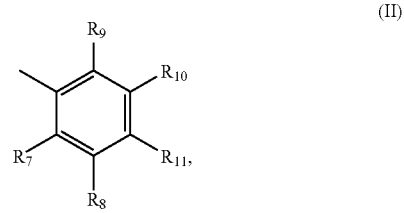

and, if n=2, $R_1$ is unsubstituted or $C_1$–$C_4$alkyl- or hydroxy-substituted phenylene or naphthylene; or —$R_{12}$—X—$R_{13}$—;

$R_2$, $R_3$, $R_4$ and $R_5$ are each independently of one another hydrogen; chloro; hydroxy; $C_1$–$C_{25}$-alkyl; $C_7$–$C_9$phenylalkyl; unsubstituted or $C_1$–$C_4$alkyl-substituted phenyl; unsubstituted or $C_1$–$C_4$alkyl-substituted $C_5$–$C_8$cycloalkyl; $C_1$–$C_{18}$alkoxy; $C_1$–$C_{18}$alkylthio; $C_1$–$C_4$alkylamino; di($C_1$–$C_4$-alkyl)amino; $C_1$–$C_{25}$alkanoyloxy; $C_1$–$C_{25}$alkanoylamino; $C_3$–$C_{25}$alkenoyloxy; $C_3$–$C_{25}$alkanoyloxy which is interrupted by oxygen, sulphur or

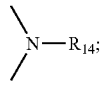

$C_6$–$C_9$cycloalkylcarbonoyloxy; benzoyloxy or $C_1$–$C_{12}$alkyl-substituted benzoyloxy; or $R_2$ and $R_3$, or $R_3$ and $R_4$, or $R_4$ and $R_5$, together with the linking carbon atoms, form a benzene ring;

or $R_4$ is —$C_mH_{2m}$—$COR_{15}$, —O—($C_vH_{2v}$)—$COR'_{15}$, —O—$(CH_2)_q$—$OR_{32}$, —$OCH_2$—$CH(OH)$—$CH_2$—$R'_{15}$, —$OCH_2$—$CH(OH)$—$CH_2$—$OR_{32}$, or —$(CH_2)_q$ OH;

or, if $R_3$, $R_5$ and $R_6$ are hydrogen, $R_4$ is additionally a radical of formula III

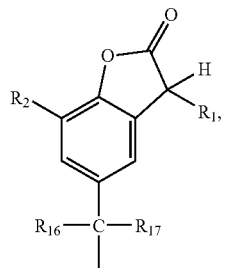

(III)

wherein $R_1$ is as defined above for n=1;

$R_6$ is hydrogen or, when $R_4$ is hydroxy, $R_6$ can also be $C_1$–$C_{25}$alkyl or $C_3$–$C_{25}$alkenyl;

$R_7$ and $R_8$ are each independently of one another hydrogen; halogen; $C_1$–$C_{25}$alkyl; $C_2$–$C_{25}$alkyl which is interrupted by oxygen, sulphur or

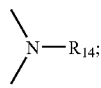

$C_1$–$C_{25}$alkylthio; $C_3$–$C_{25}$-alkenyl; $C_3$–$C_{25}$alkenyloxy; $C_3$–$C_{25}$alkynyl; $C_3$–$C_{25}$alkynyloxy; $C_7$–$C_9$phenylalkyl; $C_7$–$C_9$phenylalkoxy; unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; $C_1$–$C_4$alkylamino; di($C_1$–$C_4$alkyl)amino; $C_1$–$C_{25}$alkanoyl; $C_3$–$C_{25}$alkanoyl which is interrupted by oxygen, sulphur or

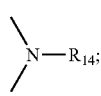

$C_1$–$C_{25}$alkanoylamino; $C_3$–$C_{25}$alkenoyl; $C_3$–$C_{25}$alkenoyl which is interrupted by oxygen, sulphur or

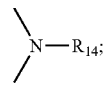

$C_3$–$C_{25}$alkenoyloxy; $C_3$–$C_{25}$alkenoyloxy which is interrupted by oxygen, sulphur or

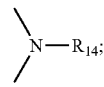

$C_6$–$C_9$cycloalkylcarbonyl; $C_6$–$C_9$cycloalkylcarbonyloxy; benzoyl or $C_1$–$C_{12}$alkyl-substituted benzoyl; benzoyloxy or $C_1$–$C_{12}$alkyl-substituted benzoyloxy;

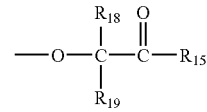

or

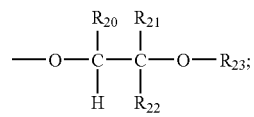

$R_8$, $R_{10}$ and $R_{11}$ are each independently of one another hydrogen; halogen; hydroxy; $C_1$–$C_{25}$alkyl; $C_2$–$C_{25}$alkyl which is interrupted by oxygen, sulphur or

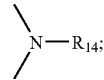

$C_1$–$C_{25}$alkoxy; $C_2$–$C_{25}$alkoxy which is interrupted by oxygen, sulphur or

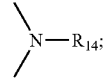

$C_1$–$C_{25}$alkylthio; $C_3$–$C_{25}$-alkenyl; $C_3$–$C_{25}$alkenyloxy; $C_3$–$C_{25}$alkynyl; $C_3$–$C_{25}$alkynyloxy; $C_7$–$C_9$phenylalkyl; $C_7$–$C_9$phenylalkoxy; unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; $C_1$–$C_4$alkylamino; di($C_1$–$C_4$alkyl)amino; $C_1$–$C_{25}$alkanoyl; $C_3$–$C_{25}$alkanoyl which is interrupted by oxygen, sulphur or

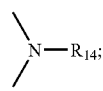

$C_1$–$C_{25}$alkanoyloxy; $C_3$–$C_{25}$alkanoyloxy which is interrupted by oxygen, sulphur or

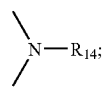

$C_1$–$C_{25}$alkanoylamino; $C_3$–$C_{25}$alkenoyl; $C_3$–$C_{25}$alkenoyl which is interrupted by oxygen, sulphur or

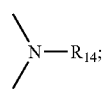

$C_3$–$C_{25}$alkenoyloxy; $C_3$–$C_{25}$alkenoyloxy which is interrupted by oxygen, sulphur or

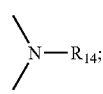

$C_6$–$C_9$cycloalkylcarbonyl;
$C_6$–$C_9$cycloalkylcarbonyloxy; benzoyl or $C_1C_{12}$alkyl-substituted benzoyl; benzoyloxy or $C_1$–$C_{12}$alkyl-substituted benzoyloxy;

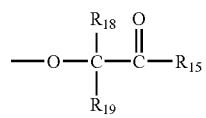

or

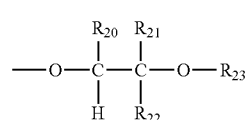

or, in formula II, $R_7$ and $R_8$, or $R_8$ and $R_{11}$, together with the linking carbon atoms, form a benzene ring;
$R_{12}$ and $R_{13}$ are each independently of the other unsubstituted or $C_1$–$C_4$alkyl-substituted phenylene or naphthylene;
$R_{14}$ is hydrogen or $C_1$–$C_8$alkyl;
$R_{15}$ and $R'_{15}$ independently are hydroxy;

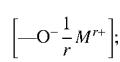

$C_1$–$C_{20}$alkoxy; $C_3$–$C_{20}$alkoxy interrupted by O and/or substituted by a radical selected from OH, phenoxy, $C_7$–$C_{15}$alkylphenoxy, $C_7$–$C_{15}$alkoxyphenoxy; or are $C_5$–$C_{12}$cycloalkoxy; $C_7$–$C_{17}$phenylalkoxy; phenoxy;

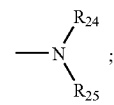

or a group of the formula IIIa or IIIb

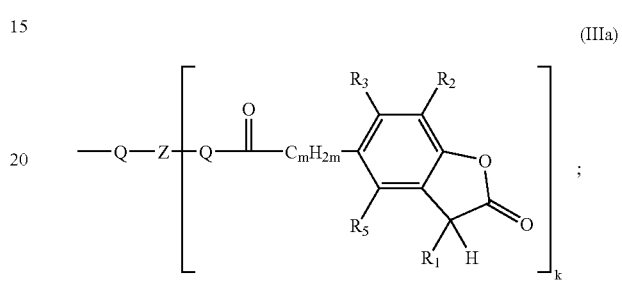

(IIIa)

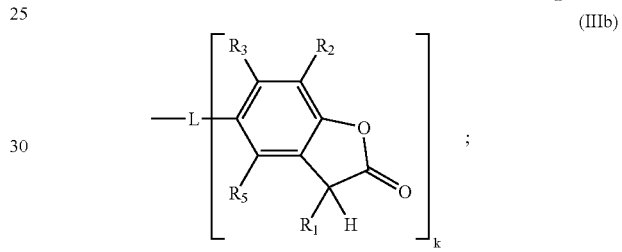

(IIIb)

$R_{16}$ and $R_{17}$ are each independently of the other hydrogen, $CF_3$, $C_1$–$C_{12}$alkyl or phenyl, or $R_{16}$ and $R_{17}$, together with the linking carbon atom, are a $C_5$–$C_8$cycloalkylidene ring which is unsubstituted or substituted by 1 to 3 $C_1$–$C_4$alkyl;
$R_{18}$ and $R_{19}$ are each independently of the other hydrogen, $C_1$–$C_4$alkyl or phenyl;
$R_{20}$ is hydrogen or $C_1$–$C_4$alkyl;
$R_{21}$ is hydrogen; unsubstituted or $C_1$–$C_4$alkyl-substituted phenyl; $C_1$–$C_{25}$alkyl; $C_2$–$C_{25}$alkyl which is interrupted by oxygen, sulphur or

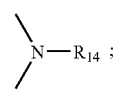

$C_7$–$C_9$phenylalkyl which is unsubstituted or substituted at the phenyl moiety by 1 to 3 $C_1$–$C_4$alkyl; $C_7$–$C_{25}$phenylalkyl which is interrupted by oxygen, sulphur or

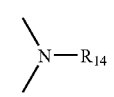

and which is unsubstituted or substituted at the phenyl moiety by 1 to 3 $C_1$–$C_4$alkyl; or $R_{20}$ and $R_{21}$, together with the linking carbon atoms, form a $C_5$–$C_{12}$cycloalkylene ring which is unsubstituted or substituted by 1 to 3 $C_1$–$C_4$alkyl;

$R_{22}$ is hydrogen or $C_1$–$C_4$alkyl;

$R_{23}$ is hydrogen; $C_1$–$C_{25}$alkanoyl; $C_3$–$C_{25}$alkenoyl; $C_3$–$C_{25}$alkanoyl which is interrupted by oxygen, sulphur or

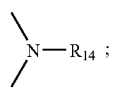

$C_2$–$C_{25}$alkanoyl which is substituted by a di($C_1$–$C_6$alkyl)phosphonate group; $C_6$–$C_9$cycloalkylcarbonyl; thenoyl; furoyl; benzoyl or $C_1$–$C_{12}$alkyl-substituted benzoyl;

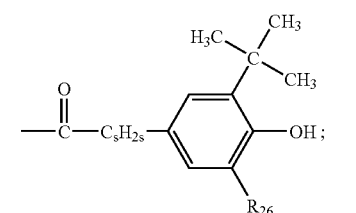

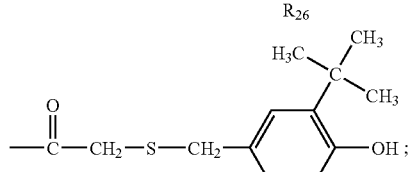

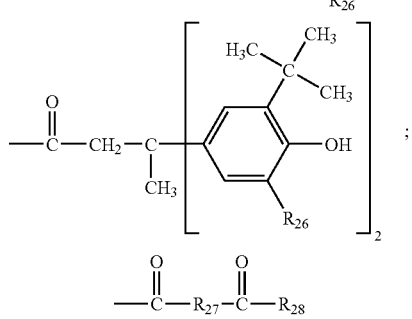

or

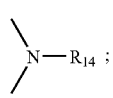

$R_{24}$ and $R_{25}$ are each independently of the other hydrogen or $C_1$–$C_{18}$alkyl;

$R_{26}$ is hydrogen or $C_1$–$C_8$alkyl;

$R_{27}$ is a direct bond; $C_1$–$C_{18}$alkylene; $C_2$–$C_{18}$alkylene which is interrupted by oxygen, sulphur or

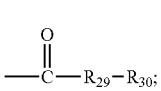

$C_2$–$C_{18}$alkenylene; $C_2$–$C_{20}$alkylidene; $C_7$–$C_{20}$phenylalkylidene; $C_5$–$C_8$cycloalkylene; $C_7$–$C_8$bicycloalkylene; unsubstitued or $C_1$–$C_4$alkyl-substituted phenylene;

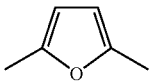

or

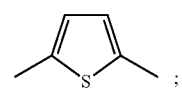

$R_{28}$ is hydroxy, $$\left[-O-\frac{1}{r}M^{r+}\right],$$

$C_1$–$C_{18}$alkoxy or

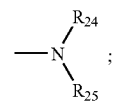

$R_{29}$ is oxygen or —NH—;

$R_{30}$ is $C_1$–$C_{18}$alkyl or phenyl;

$R_{31}$ is hydrogen or $C_1$–$C_{18}$alkyl;

$R_{32}$ is $C_1$–$C_{18}$alkanoyl; $C_1$–$C_8$alkanoyl substituted by phenyl or $C_7$–$C_{15}$alkylphenyl; $C_3$–$C_{18}$alkenoyl; cyclohexylcarbonyl; or naphthylcarbonyl;

L is a linking group of valency (k+1) and is as a divalent group

—O—;

Q—$C_2$–$C_{12}$alkylene-Q;

—O—$CH_2$—CH(OH)—$CH_2$—O—;

—Q—$C_2$–$C_{12}$alkylene-Q—CO—$C_vH_{2v}$—O—;

—O—$C_2$–$C_{12}$alkylene-O—$CH_2$—CH(OH)—$CH_2$—O—;

Q-phenylene-Q or

Q-phenylene-D-phenylene-Q with D being $C_1$–$C_4$alkylene, O, S, SO or $SO_2$;

L as a trivalent group is Q-capped $C_3$–$C_{12}$alkanetriyl, a trivalent residue of a hexose or a hexitol, or a group (—O—$CH_2$)$_3$C—$CH_2$OH; —Q—$C_aH_{2a}$—N($C_bH_{2b}$—Q—)—$C_cH_{2c}$—Q—;

—Q—$C_3$–$C_{12}$alkanetriyl(—Q—CO—$C_vH_{2v}$—O—)$_2$;

—O—$C_3$–$C_{12}$alkanetriyl(—O—$CH_2$—CH(OH)—$CH_2$—O—)$_2$; and

L as a tetravalent group is a tetravalent residue of a hexose or a hexitol;

—Q—$C_4$–$C_{12}$alkanetetryl(—Q—CO—$C_vH_{2v}$—O—)$_3$;

—O—$C_4$–$C_{12}$alkanetetryl(—O—$CH_2$—CH(OH)—$CH_2$—O—)$_3$; Q-capped $C_4$–$C_{12}$alkanetetryl; a group

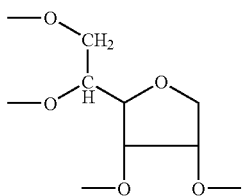

or a group

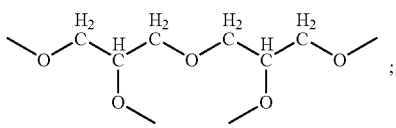

M is an r-valent metal cation;
Q is oxygen or —NH—;
X is a direct bond, oxygen, sulphur or —NR$_{31}$—;
Z is a linking group of valency (k+1) and is as a divalent group $C_2$–$C_{12}$alkylene; Q-interrupted $C_4$–$C_{12}$alkylene; phenylene or phenylene-D-phenylene with D being $C_1$–$C_4$alkylene, O, S, SO or SO$_2$;
Z as a trivalent group is $C_3$–$C_{12}$alkanetriyl, a trivalent residue of a hexose or a hexitol, a group (—CH$_2$)$_3$C—CH$_2$OH, or a group —C$_a$H$_{2a}$—N(C$_b$H$_{2b}$—)—C$_c$H$_{2c}$—; and
Z as a tetravalent group is a tetravalent, carbon-ended residue of a hexose or a hexitol, $C_4$–$C_{12}$alkanetetryl, a group

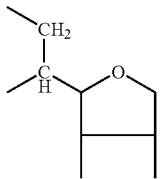

or a group

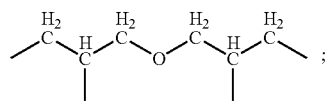

a, b, c and k independently are 1, 2 or 3;
m is 0 or a number from the range 1–12;
n is 1 or 2;
q is 1, 2, 3, 4, 5 or 6;
r is 1, 2 or 3; and
s is 0, 1 or 2;
v is 1, 2, 3, 4, 5, 6, 7 or 8;
provided that, when R$_7$ is hydroxy, alkanoyloxy or alkanoyloxy interrupted by O, S or N(R$_{14}$) and R$_9$ is hydrogen, R$_{10}$ is not identical with R$_4$; and when R$_9$ is hydroxy, alkanoyloxy or alkanoyloxy interrupted by O, S or N(R$_{14}$) and R$_7$ is hydrogen, R$_8$ is not identical with R$_4$, into an interlayer between the light sensitive silver halide emulsion layers thus scavenging the oxidized form of developer when migrating from the light sensitive silver halide emulsion layer in which it has been formed to the interlayer.

2. Process according to claim 1, wherein in the compound of formula I R$_7$ and R$_9$ are each independently of one another hydrogen; halogen; $C_1$–$C_{25}$alkyl; $C_2$–$C_{25}$alkyl which is interrupted by oxygen, sulphur or

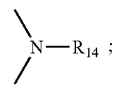

$C_2$–$C_{25}$alkoxy which is interrupted by oxygen, sulphur or

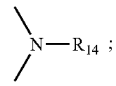

$C_1$–$C_{25}$alkylthio; $C_3$–$C_{25}$alkenyl; $C_3$–$C_{25}$alkenyloxy; $C_3$–$C_{25}$alkynyl; $C_3$–$C_{25}$alkynyloxy; $C_7$–$C_9$phenylalkyl; $C_7$–$C_9$phenylalkoxy; unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; $C_1$–$C_4$alkylamino; di($C_1$–$C_4$alkyl)amino; $C_1$–$C_{25}$alkanoyl; $C_3$–$C_{25}$alkanoyl which is interrupted by oxygen, sulphur or

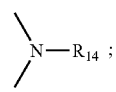

$C_1$–$C_{25}$alkanoylamino; $C_3$–$C_{25}$alkenoyl; $C_3$–$C_{25}$alkenoyl which is interrupted by oxygen, sulphur or

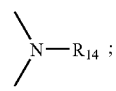

$C_6$–$C_9$cycloalkylcarbonyl; benzoyl or $C_1$–$C_{12}$alkyl-substituted benzoyl;

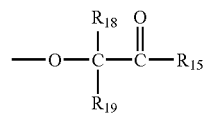

or

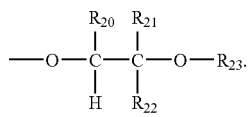

3. Process according to claim 1 wherein in the compound of formula I R$_1$ is naphthyl, phenanthryl, anthryl, 5,6,7,8-tetrahydro-2-naphthyl, 5,6,7,8-tetrahydro-1-naphthyl, thienyl, benzo[b]thienyl, naphtho[2,3-b]thienyl, thianthrenyl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, □-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by $C_1$–$C_4$alkyl, $C_1$–$C_4$alkoxy, $C_1$–$C_4$alkylthio, hydroxy, halogen, amino, $C_1$–$C_4$alkylamino, phenylamino or di($C_1$–$C_4$-alkyl)amino, or $R_1$ is a radical of formula II

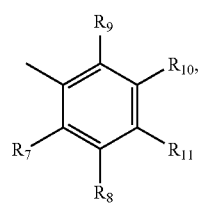

(II)

and, if n=2, $R_1$ is unsubstituted or $C_1$–$C_4$alkyl- or hydroxy-substituted phenylene or naphthylene; or —$R_{12}$—X—$R_{13}$—;

$R_2$, $R_3$, $R_4$ and $R_5$ are each independently of one another hydrogen, chloro, hydroxy, $C_1$–$C_{25}$-alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di($C_1$–$C_4$-alkyl)amino, $C_1$–$C_{25}$alkanoyloxy, $C_1$–$C_{25}$alkanoylamino, $C_3$–$C_{25}$alkenoyloxy; $C_3$–$C_{25}$alkanoyloxy which is interrupted by oxygen, sulphur or

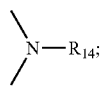

$C_6$–$C_9$cycloalkylcarbonoyloxy, benzoyloxy or $C_1$–$C_{12}$alkyl-substituted benzoyloxy; or $R_2$ and $R_3$, or $R_3$ and $R_4$, or $R_4$ and $R_5$, together with the linking carbon atoms, form a benzene ring; or $R_4$ is —$C_mH_{2m}$—$COR_{15}$ or —$(CH_2)_q$OH or, if $R_3$, $R_5$ and $R_6$ are hydrogen, $R_4$ is additionally a radical of formula III

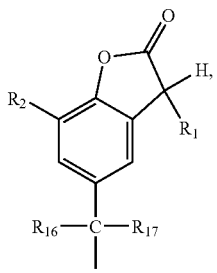

(III)

wherein $R_1$ is as defined above for n=1;

$R_6$ is hydrogen or, when $R_4$ is hydroxy, $R_6$ can also be $C_1$–$C_{25}$alkyl or $C_3$–$C_{25}$alkenyl;

$R_7$, $R_8$, $R_9$, $R_{10}$ and $R_{11}$ are each independently of one another hydrogen, halogen, hydroxy, $C_1$–$C_{25}$alkyl; $C_2$–$C_{25}$alkyl which is interrupted by oxygen, sulphur or

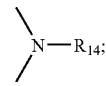

$C_1$–$C_{25}$alkoxy; $C_2$–$C_{25}$alkoxy which is interrupted by oxygen, sulphur or

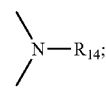

$C_1$–$C_{25}$alkylthio, $C_3$–$C_{25}$-alkenyl, $C_3$–$C_{25}$alkenyloxy, $C_3$–$C_{25}$alkynyl, $C_3$–$C_{25}$alkynyloxy, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; $C_1$–$C_4$alkylamino, di($C_1$–$C_4$alkyl)amino; $C_1$–$C_{25}$alkanoyl; $C_3$–$C_{25}$alkanoyl which is interrupted by oxygen, sulphur or

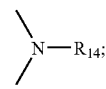

$C_1$–$C_{25}$alkanoyloxy; $C_3$–$C_{25}$alkanoyloxy which is interrupted by oxygen, sulphur or

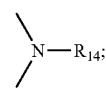

$C_1$–$C_{25}$alkanoylamino, $C_3$–$C_{25}$alkenoyl; $C_3$–$C_{25}$alkenoyl which is interrupted by oxygen, sulphur or

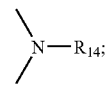

$C_3$–$C_{25}$alkenoyloxy; $C_3$–$C_{25}$alkenoyloxy which is interrupted by oxygen, sulphur or

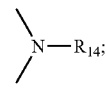

$C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

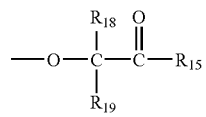

or

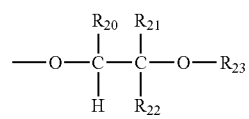

or, in formula II, $R_7$ and $R_8$, or $R_8$ and $R_{11}$, together with the linking carbon atoms, form a benzene ring, $R_{12}$ and $R_{13}$ are each independently of the other unsubstituted or $C_1$–$C_4$alkyl-substituted phenylene or naphthylene, $R_{14}$ is hydrogen or $C_1$–$C_8$alkyl, $R_{15}$ is hydroxy,

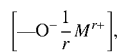

$C_1$–$C_{20}$alkoxy,

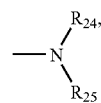

or a group of the formula IIIa

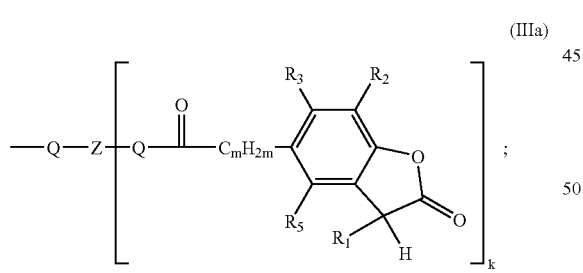

$R_{16}$ and $R_{17}$ are each independently of the other hydrogen, $CF_3$, $C_1$–$C_{12}$alkyl or phenyl, or $R_{16}$ and $R_{17}$, together with the linking carbon atom, are a $C_5$–$C_8$cycloalkylidene ring which is unsubstituted or substituted by 1 to 3 $C_1$–$C_4$alkyl;

$R_{18}$ and $R_{19}$ are each independently of the other hydrogen, $C_1$–$C_4$alkyl or phenyl, $R_{20}$ is hydrogen or $C_1$–$C_4$alkyl, $R_{21}$ is hydrogen, unsubstituted or $C_1$–$C_4$alkyl-substituted phenyl; $C_1$–$C_{25}$alkyl; $C_2$–$C_{25}$alkyl which is interrupted by oxygen, sulphur or

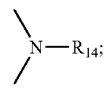

$C_7$–$C_9$phenylalkyl which is unsubstituted or substituted at the phenyl moiety by 1 to 3 $C_1$–$C_4$alkyl; $C_7$–$C_{25}$phenylalkyl which is interrupted by oxygen, sulphur or

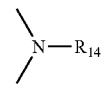

and which is unsubstituted or substituted at the phenyl moiety by 1 to 3 $C_1$–$C_4$alkyl, or $R_{20}$ and $R_{21}$, together with the linking carbon atoms, form a $C_5$–$C_{12}$cycloalkylene ring which is unsubstituted or substituted by 1 to 3 $C_1$–$C_4$alkyl;

$R_{22}$ is hydrogen or $C_1$–$C_4$alkyl, $R_{23}$ is hydrogen, $C_1$–$C_{25}$alkanoyl, $C_3$–$C_{25}$alkenoyl; $C_3$–$C_{25}$alkanoyl which is interrupted by oxygen, sulphur or

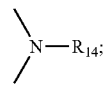

$C_2$–$C_{25}$alkanoyl which is substituted by a di($C_1$–$C_6$alkyl)phosphonate group; $C_6$–$C_9$cycloalkylcarbonyl, thenoyl, furoyl, benzoyl or $C_1$–$C_{12}$alkyl-substituted benzoyl;

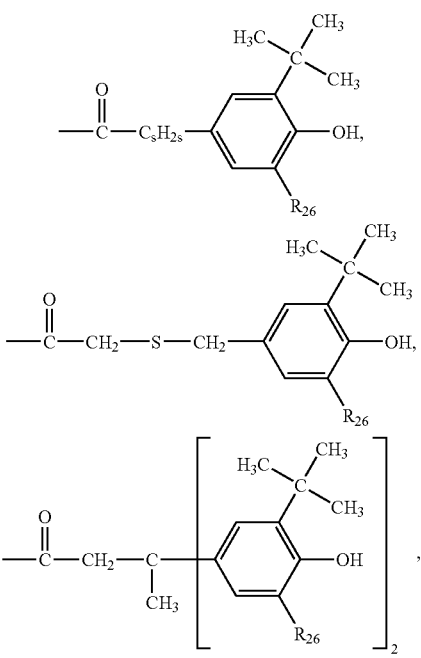

-continued

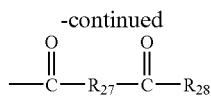

or

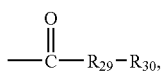

$R_{24}$ and $R_{25}$ are each independently of the other hydrogen or $C_1$–$C_{18}$alkyl,
$R_{26}$ is hydrogen or $C_1$–$C_8$alkyl,
$R_{27}$ is a direct bond, $C_1$–$C_{18}$alkylene; $C_2$–$C_{18}$alkylene which is interrupted by oxygen, sulphur or

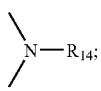

$C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

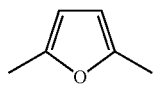

or

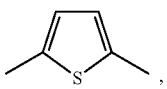

$R_{28}$ is hydroxy,

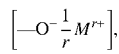

$C_1$–$C_{18}$alkoxy or

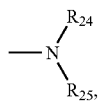

$R_{29}$ is oxygen or —NH—,
$R_{30}$ is $C_1$–$C_{18}$alkyl or phenyl,
$R_{31}$ is hydrogen or $C_1$–$C_{18}$alkyl,
M is an r-valent metal cation,
Q is oxygen or —NH—,
X is a direct bond, oxygen, sulphur or —NR$_{31}$—,
Z is a linking group of valency (k+1) and is as a divalent group $C_2$–$C_{12}$alkylene, Q-interrupted $C_4$–$C_{12}$alkylene, phenylene or phenylene-D-phenylene with D being $C_1$–$C_4$alkylene, O, S, SO or $SO_2$;

Z as a trivalent group is $C_3$–$C_{12}$alkanetriyl, a trivalent residue of a hexose or a hexitol, a group (—CH$_2$)$_3$C—CH$_2$OH, or a group —C$_a$H$_{2a}$—N(C$_b$H$_{2b}$—)—C$_c$H$_{2c}$—; and Z as a tetravalent group is a tetravalent residue of a hexose or a hexitol, $C_4$–$C_{12}$alkanetetryl, a group

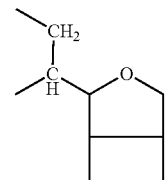

or a group

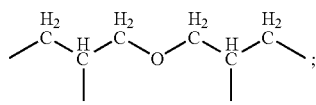

a, b, c and k independently are 1, 2 or 3,
m is 0 or a number from the range 1–12,
n is 1 or 2,
q is 1, 2, 3, 4, 5 or 6,
r is 1, 2 or 3, and
s is 0, 1 or 2;
provided that, when $R_7$ is hydroxy, alkanoyloxy or alkanoyloxy interrupted by O, S or N($R_{14}$) and $R_9$ is hydrogen, $R_{10}$ is not identical with $R_4$.

4. Process according to claim 1, wherein in the compound of formula I $R_2$, $R_3$ and $R_5$, independently are H, Cl, hydroxy, $C_1$–$C_{25}$alkyl, $C_7$–$C_9$phenylalkyl, unsubstituted or $C_1$–$C_4$alkyl-substituted phenyl; $C_1$–$C_{18}$alkoxy, $C_1$–$C_{25}$alkanoyloxy, $C_3$–$C_{25}$alkenoyloxy; and where $R_4$ is Cl, hydroxy, $C_1$–$C_{25}$alkyl, $C_7$–$C_9$phenylalkyl, unsubstituted or $C_1$–$C_4$alkyl-substituted phenyl; $C_1$–$C_{18}$alkoxy, $C_1$–$C_{25}$alkanoyloxy, $C_3$–$C_{25}$alkenoyloxy or is a group —C$_m$H$_{2m}$—COR$_{15}$, —O—(C$_v$H$_{2v}$)—COR'$_{15}$, —O—(CH$_2$)$_q$—OR$_{32}$, —OCH$_2$—CH(OH)—CH$_2$—R'$_{15}$, —OCH$_2$—CH(OH)—CH$_2$—OR$_{32}$, or where $R_3$, $R_5$ and $R_6$ are H, $R_4$ may be a residue of formula III, or where $R_8$ or $R_{10}$ are other than H, $R_4$ may also be hydrogen;
$R_6$ is H,
$R_7$ and $R_9$ are each independently of one another hydrogen; halogen; $C_1$–$C_{25}$alkyl; $C_2$–$C_{25}$alkyl which is interrupted by oxygen, sulphur or

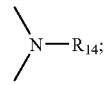

$C_3$–$C_{25}$alkenyl; $C_3$–$C_{25}$alkynyl; $C_7$–$C_9$phenylalkyl; unsubstituted or $C_1$–$C_4$alkyl-substituted phenyl; unsubstituted or $C_1$–$C_4$alkyl-substituted $C_5$–$C_8$cycloalkyl;
$R_8$, $R_{10}$ and $R_{11}$ independently are H, halogen, hydroxy, $C_1$–$C_{25}$alkyl, O interrupted $C_2$–$C_{25}$alkyl; $C_1$–$C_{25}$alkoxy, O interrupted $C_2$–$C_{25}$alkoxy; $C_3$–$C_{25}$alkenyl, $C_3$–$C_{25}$alkenyloxy, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl substituted phenoxy; unsubstituted or $C_1$–$C_4$alkyl substituted $C_5$–$C_8$ cycloalkyl; unsubstituted or $C_1$–$C_4$alkyl substituted $C_5$–$C_8$cycloalkoxy; $C_1$–$C_4$alkylamino, di-($C_1$–$C_4$-alkyl)amino, $C_1$–$C_{25}$alkanoyl, $C_1$–$C_{25}$alkanoyloxy; $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl substituted benzoyloxy;

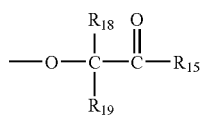

or

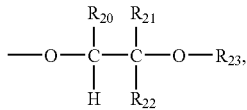

or where formula II $R_7$ and $R_8$ or $R_8$ and $R_{11}$ together with the carbon
atoms, they are bonded to, form a phenyl ring;

$R_{15}$ and $R'_{15}$ independently are $C_1$–$C_{18}$alkoxy; $C_3$–$C_{20}$alkoxy interrupted by O and/or substituted by a radical selected from OH, phenoxy, $C_7$–$C_{15}$alkylphenoxy, $C_7$–$C_{15}$alkoxyphenoxy; or are $C_5$–$C_{12}$cycloalkoxy; $C_7$–$C_{17}$phenylalkoxy; phenoxy; or —$NR_{23}R_{24}$; or a group of formula IIIa or IIIb;

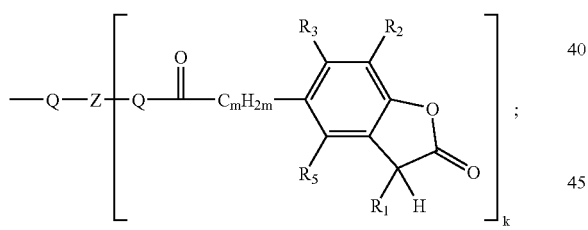
(IIIa)

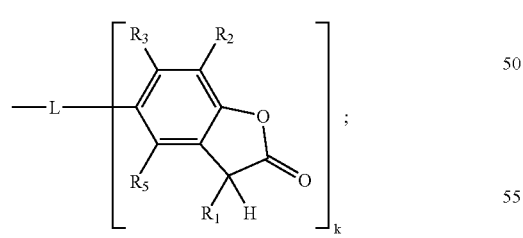
(IIIb)

$R_{16}$ and $R_{17}$ independently are H, $CF_3$, $C_1$–$C_{12}$alkyl or phenyl; or $R_{16}$ and $R_{17}$ together with the bonding carbon atom form an unsubstituted or 1–3 $C_1$–$C_4$alkyl-substituted $C_5$–$C_8$cycloalkylidene ring;

$R_{18}$ and $R_{19}$ independently are H, $C_1$–$C_4$alkyl or phenyl;

$R_{20}$ is H or $C_1$–$C_4$alkyl;

$R_{21}$ is H, unsubstituted or $C_1$–$C_4$alkyl substituted phenyl; $C_1$–$C_{25}$alkyl, unsubstituted or on the phenyl ring 1–3 $C_1$–$C_4$alkyl-substituted $C_7$–$C_9$phenylalkyl;

$R_{22}$ is H or $C_1$–$C_4$alkyl;

$R_{23}$ is H, $C_1$–$C_{25}$alkanoyl, $C_3$–$C_{25}$alkenoyl; di($C_1$–$C_6$alkyl)phosphonate-substituted $C_2$–$C_{25}$alkanoyl; $C_6$–$C_9$cycloalkylcarbonyl, thenoyl, furoyl, benzoyl or $C_1$–$C_{12}$alkyl-substituted benzoyl;

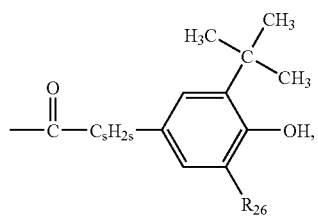

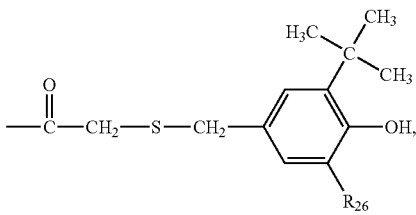

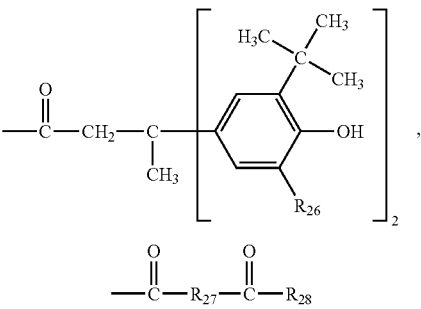

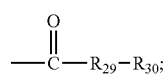

or

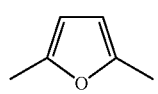

$R_{24}$ and $R_{25}$ independently are H or $C_1$–$C_{18}$alkyl;

$R_{26}$ is H or $C_1$–$C_8$alkyl;

$R_{27}$ is a direct bond, $C_1$–$C_{18}$alkylen, $C_2$–$C_{18}$alkylen, $C_7$–$C_{20}$phenylalkyliden, $C_5$–$C_8$cycloalkylen, unsubstituted or $C_1$–$C_4$alkyl-substituted phneylene,

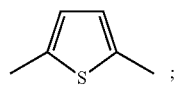

or

;

$R_{28}$ $C_1$—$C_{18}$alkoxy or

$R_{29}$ is O or —NH—;
$R_{30}$ $C_1$–$C_{18}$alkyl or phenyl;
M a metal cation of the valency r;
X a direct bond, O, S or —NR$_{31}$—;
n 1 or 2;
m is a number from the range 1–8;
q 1, 2, 3, 4, 5 or 6;
r 1, 2 or 3; and
s is 0, 1 or 2.

5. Process according to claim 1 wherein the compound of formula I corresponds to the formula IV

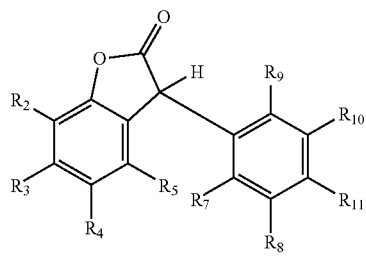

wherein
$R_2$ is H or $C_1$–$C_{20}$alkyl;
$R_3$ is H or $C_1$–$C_{18}$alkyl;
$R_4$ is $C_1$–$C_8$alkyl, H, $C_1$–$C_6$alkoxy or a group —$C_mH_{2m}$—COR$_{15}$; —O—($C_vH_{2v}$)—COR$_{15}$, —O—($CH_2$)$_q$—OR$_{32}$; —OCH$_2$—CH(OH)—CH$_2$—R$_{15}$; —OCH$_2$—CH(OH)—CH$_2$—OR$_{32}$; or a group of the formula III;

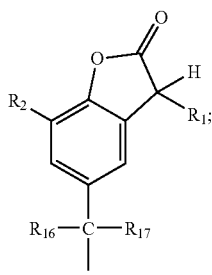

$R_5$ is H or $C_1$–$C_{18}$alkyl;
$R_7$ and $R_9$ are each independently of one another hydrogen; halogen; $C_1$–$C_{25}$alkyl; $C_3$–$C_{25}$alkenyl; $C_3$–$C_{25}$alkynyl; $C_7$–$C_9$phenylalkyl; unsubstituted or $C_1$–$C_4$alkyl-substituted phenyl; unsubstituted or $C_1$–$C_4$alkyl-substituted $C_5$–$C_8$cycloalkyl;
$R_8$, $R_{10}$ and $R_{11}$ independently are H, OH, chloro, $C_1$–$C_{18}$alkyl, $C_1$–$C_{18}$alkoxy, di($C_1$–$C_4$alkyl)amino, $C_7$–$C_9$phenylalkyl; unsubstituted or $C_1$–$C_4$alkyl-substituted phenyl; unsubstituted or $C_1$–$C_4$alkyl-substituted $C_5$–$C_8$cycloalkyl; $C_2$–$C_{18}$alkanoyloxy, $C_3$–$C_{18}$-alkoxycarbonylalkoxy or

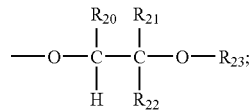

$R_{15}$ is $C_1$–$C_{18}$alkoxy; $C_3$–$C_{20}$alkoxy interrupted by O; or are cyclohexyloxy; $C_7$–$C_{17}$phenylalkoxy; phenoxy; or a group of formula IIIa or IIIb;

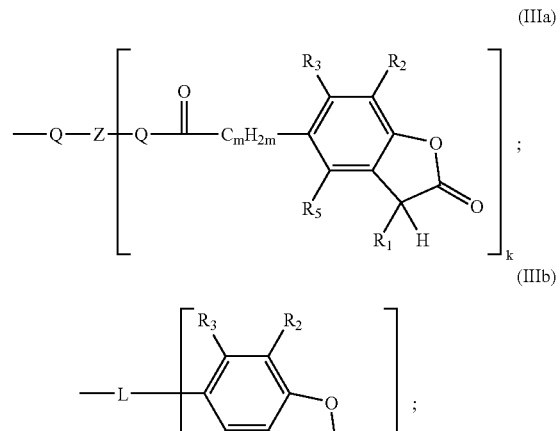

$R_{16}$ and $R_{17}$ independently are H, $C_1$–$C_{12}$alkyl or phenyl; or $R_{16}$ and $R_{17}$ together with the bonding carbon atom form a $C_5$–$C_8$cycloalkylidene ring;
$R_{20}$, $R_{21}$ and $R_{22}$ independently are H or $C_1$–$C_4$alkyl;
$R_{23}$ is H, $C_2$–$C_{18}$alkanoyl or a group

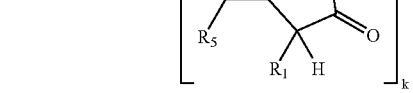

$R_{26}$ is $C_1$–$C_4$alkyl;
$R_{32}$ is $C_1$–$C_{18}$alkanoyl; $C_1$–$C_8$alkanoyl substituted by phenyl or $C_7$–$C_{15}$alkylphenyl; $C_3$–$C_{18}$alkenoyl; cyclohexylcarbonyl; or naphthylcarbonyl;
L is a divalent group —O—; Q—$C_2$–$C_{12}$alkylene-Q; —O—CH$_2$—CH(OH)—CH$_2$—O—; —Q—$C_2$–$C_{12}$alkylene-Q—CO—$C_vH_{2v}$—O—; —O—$C_2$–$C_{12}$alkylene-O—CH$_2$—CH(OH)—CH$_2$—O—;
Q is oxygen;
Z is $C_2$–$C_{12}$alkylene;
k is 1;
m is 1, 2, 3, 4, 5 or 6;
v is 1 or 2; and
s is 0, 1 or 2.

6. Process according to claim 5 wherein in the compound of formula IV
    $R_2$ is $C_1$–$C_{20}$alkyl;
    $R_3$ is H or $C_1$–$C_{18}$alkyl;
    $R_4$ is $C_1$–$C_6$alkyl, $C_1$–$C_6$alkoxy or a group —$C_mH_{2m}$—$COR_{15}$ or a group of the formula III

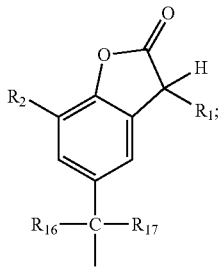

$R_5$ is H or $C_1$–$C_{18}$alkyl;
$R_7$ and $R_9$ independently are H, chloro, $C_1$–$C_{18}$alkyl;
$R_8$, $R_{10}$ and $R_{11}$ independently are H, OH, chloro, $C_1$–$C_{18}$alkyl, $C_1$–$C_{18}$alkoxy, di($C_1$–$C_4$alkyl)amino, phenyl, $C_2$–$C_{18}$alkanoyloxy or

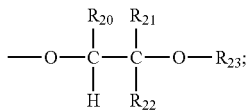

$R_{15}$ is $C_1$–$C_{18}$alkoxy or a group of the formula IIIa

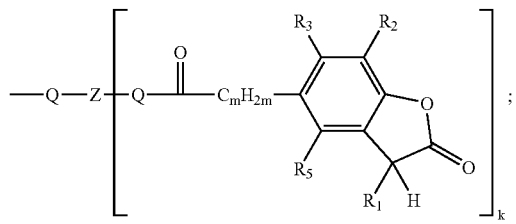

$R_{20}$, $R_{21}$ and $R_{22}$ are H;
$R_{23}$ is H, $C_2$–$C_{18}$alkanoyl or a group

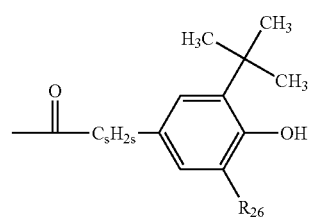

$R_{26}$ is $C_1$–$C_4$alkyl;
Q is oxygen;
Z is $C_2$–$C_{12}$alkylene;

k is 1;
m is 1, 2, 3, 4, 5 or 6 and
s is 0, 1 or 2.

7. Process according to claim 5 wherein in the compound of formula IV, $R_4$ is $C_1$–$C_6$alkyl, or a group of —$C_mH_{2m}$—$COR_{15}$, —O—($C_vH_{2v}$)—$COR_{15}$, —O—($CH_2$)$_q$—$OR_{32}$, —$OCH_2$—$CH(OH)$—$CH_2$—$R_{15}$, —$OCH_2$—$CH(OH)$—$CH_2$—$OR_{32}$, or a group of the formula III.

8. Process according to claim 1, wherein the compound of formula I is incorporated into the colour photographic material in an amount from 10 to 1000 mg/m².

9. Process according to claim 1, wherein the compound of formula I is concentrated in one or more interlayers separating light sensitive layers of the colour photographic material.

10. Process according to claim 9, wherein a green-sensitive layer containing a magenta coupler of the pyrazolo-azole class is adjacent to an interlayer containing the compound of formula I.

11. A colour photographic material or digital recording material containing a compound of the formula IV

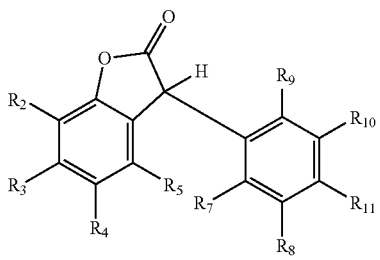

wherein
    $R_2$ is H or $C_1$–$C_{20}$alkyl;
    $R_3$ is H or $C_1$–$C_{18}$alkyl;
    $R_4$ is $C_1$–$C_8$alkyl, $C_1$–$C_6$alkoxy or a group —$C_mH_{2m}$—$COR_{15}$; —O—($C_vH_{2v}$)—$COR_{15}$; —O—($CH_2$)$_q$—$OR_{32}$; —$OCH_2$—$CH(OH)$—$CH_2$—$R_{15}$; —$OCH_2$—$CH(OH)$—$CH_2$—$OR_{32}$; or a group of the formula III;

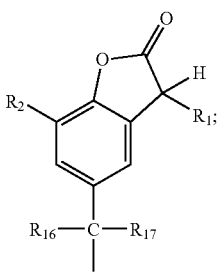

$R_5$ is H or $C_1$–$C_{18}$alkyl;
$R_7$ and $R_9$ independently are H, chloro, $C_1$–$C_{18}$alkyl or phenyl;

$R_8$, $R_{10}$ and $R_{11}$ independently are H, OH, chloro, $C_1$–$C_{18}$alkyl, $C_1$–$C_{18}$alkoxy, di($C_1$–$C_4$alkyl)amino, phenyl, $C_2$–$C_{18}$alkanoyloxy, $C_3$–$C_{18}$-alkoxycarbonylalkoxy or

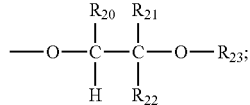

$R_{15}$ is $C_1$–$C_{18}$alkoxy; $C_3$–$C_{20}$alkoxy interrupted by O; or are cyclohexyloxy; $C_7$–$C_{17}$phenylalkoxy; phenoxy; or a group of formula IIIa or IIIb;

(IIIa)

(IIIb)

$R_{16}$ and $R_{17}$ independently are H, $C_1$–$C_{12}$alkyl or phenyl; or $R_{16}$ and $R_{17}$ together with the bonding carbon atom form a $C_5$–$C_8$cycloalkylidene ring;
$R_{20}$, $R_{21}$ and $R_{22}$ independently are H or $C_1$–$C_4$alkyl;
$R_{23}$ is H, $C_2$—$C_{18}$alkanoyl or a group

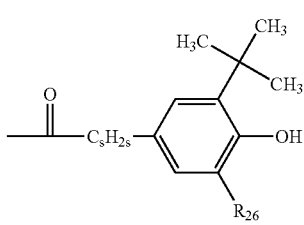

$R_{26}$ is $C_1$–$C_4$alkyl;
$R_{32}$ is $C_1$–$C_{18}$alkanoyl; $C_1$–$C_8$alkanoyl substituted by phenyl or $C_7$–$C_{15}$alkylphenyl; $C_3$–$C_{18}$alkenoyl; cyclohexylcarbonyl; or naphthylcarbonyl;
L is a divalent group —O—; Q—$C_2$–$C_{12}$alkylene-Q; —O—$CH_2$—CH(OH)—$CH_2$—O—; —Q—$C_2$–$C_{12}$alkylene-Q—CO—$C_vH_{2v}$—O—; —O—$C_2$–$C_{12}$alkylene-O—$CH_2$—CH(OH)—$CH_2$—O—;
Q is oxygen;
Z is $C_2$–$C_{12}$alkylene;
k is 1;
m is 1, 2, 3, 4, 5 or 6;

v is 1 or 2 and
s is 0, 1 or 2.

12. Compound of the formula V

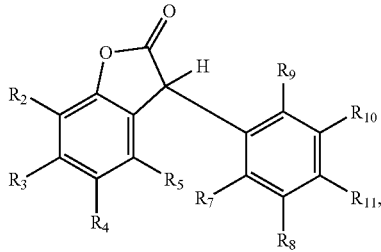

wherein
$R_4$ is —O—($C_vH_{2v}$)—$COR_{15}$; —O—$(CH_2)_q$—$OR_{32}$; —$OCH_2$—CH(OH)—$CH_2$—$R_{15}$; or —$OCH_2$—CH(OH)—$CH_2$—$OR_{32}$;
$R_{15}$ is hydroxy,

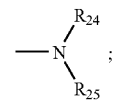

$C_1$–$C_{20}$alkoxy; $C_3$–$C_{20}$alkoxy interrupted by O and/or substituted by a radical selected from OH, phenoxy, $C_7$–$C_{15}$alkylphenoxy, $C_7$–$C_{15}$alkoxyphenoxy; or $R_{15}$ is $C_5$–$C_{12}$cycloalkoxy; $C_7$–$C_{17}$phenylalkoxy; phenoxy;

$$-N\begin{matrix}R_{24}\\R_{25}\end{matrix};$$

or a group of the formula IIIa or IIIb;

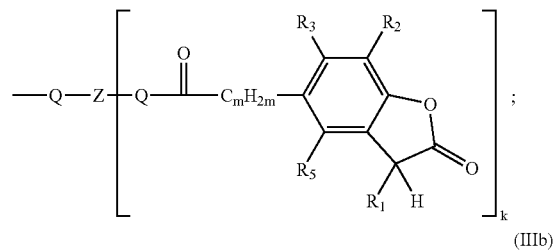

$R_{32}$ is $C_1$–$C_{18}$alkanoyl; $C_1$–$C_8$alkanoyl substituted by phenyl or $C_7$–$C_{15}$alkylphenyl; $C_3$–$C_{18}$alkenoyl; cyclohexylcarbonyl; or naphthylcarbonyl;
L is a linking group of valency (k+1) and is, as a divalent group, —O—; Q—$C_2$–$C_{12}$alkylene-Q; —O—$CH_2$—

CH(OH)—CH$_2$—O—; —Q—C$_2$–C$_{12}$alkylene-Q—CO—C$_v$H$_{2v}$—O—; —O—C$_2$–C$_{12}$alkylene-O—CH$_2$—CH(OH)—CH$_2$—O—; Q-phenylene-Q or Q-phenylene-D-phenylene-Q with D being C$_1$–C$_4$alkylene, O, S, SO or SO$_2$;

L, as a trivalent group, is Q-capped C$_3$–C$_{12}$alkanetriyl, a trivalent residue of a hexose or a hexitol, or a group (—O—CH$_2$)$_3$C—CH$_2$OH; —Q—C$_a$H$_{2a}$—N(C$_b$H$_{2b}$—Q—)—C$_c$H$_{2c}$—Q—; —Q—C$_3$–C$_{12}$alkanetriyl(—Q—CO—C$_v$H$_{2v}$—O—)$_2$; —O—C$_3$–C$_{12}$alkanetriyl(—O—CH$_2$—CH(OH)—CH$_2$—O—)$_2$; and L, as a tetravalent group, is a tetravalent residue of a hexose or a hexitol; —Q—C$_4$–C$_{12}$alkanetetryl(—Q—CO—C$_v$H$_{2v}$—O—)$_3$; —O—C$_4$–C$_{12}$alkanetetryl(—O—CH$_2$—CH(OH)—CH$_2$—O—)$_3$; Q-capped C$_4$–C$_{12}$alkanetetryl; a group

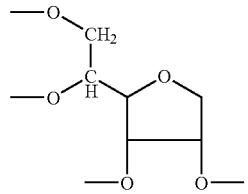

or a group

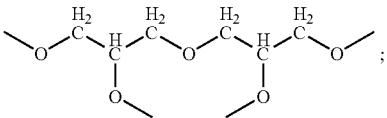

Q is oxygen or —NH—;

Z is a linking group of valency (k+1) and is as a divalent group C$_2$–C$_{12}$alkylene, Q-interrupted C$_4$–C$_{12}$alkylene, phenylene or phenylene-D-phenylene with D being C$_1$–C$_4$alkylene, O, S, SO or SO$_2$;

Z, as a trivalent group, is C$_3$–C$_{12}$alkanetriyl, a trivalent residue of a hexose or a hexitol, a group (—CH$_2$)$_3$C—CH$_2$OH, or a group —C$_a$H$_{2a}$—N(C$_b$H$_{2b}$—)—C$_c$H$_{2c}$—; and Z, as a tetravalent group, is a tetravalent residue of a hexose or a hexitol, C$_4$–C$_{12}$alkanetetryl, a group

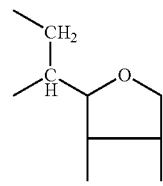

or a group

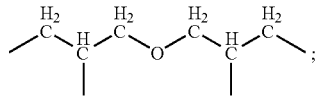

a, b, c and k independently are 1, 2 or 3, m is 0 or a number from the range 1–12, s is 1 or 2, v is 1, 2, 3, 4, 5, 6, 7 or 8;

and all other residues are as defined in claim 1 for formula I if n is 1.

13. Process for stabilizing an organic material against deterioration by light, oxygen and/or heat, which process comprises incorporating a compound of the formula V according to claim 12 as stabilizer into said organic material.

* * * * *